(12) United States Patent
Görgens et al.

(10) Patent No.: US 10,513,496 B2
(45) Date of Patent: *Dec. 24, 2019

(54) AMINOBENZAMIDE DERIVATIVES AS USEFUL AGENTS FOR CONTROLLING ANIMAL PARASITES

(71) Applicant: BAYER INTELLECTUAL PROPERTY GMBH, Monheim am Rhein (DE)

(72) Inventors: Ulrich Görgens, Ratingen (DE); Akihiko Yanagi, Oyama (JP); Katsuaki Wada, Oyama (JP); Tetsuya Murata, Oyama (JP); Yukiyoshi Watanabe, Tokyo (JP); Jun Mihara, Oyama (JP); Koichi Araki, Ushiku (JP)

(73) Assignee: Bayer Animal Health GmbH, Monheim am Rhein (DE)

(*) Notice: Subject to any disclaimer, the term of this patent is extended or adjusted under 35 U.S.C. 154(b) by 0 days.

This patent is subject to a terminal disclaimer.

(21) Appl. No.: 15/938,900

(22) Filed: Mar. 28, 2018

(65) Prior Publication Data

US 2018/0215713 A1    Aug. 2, 2018

Related U.S. Application Data

(62) Division of application No. 13/456,880, filed on Apr. 26, 2012, now Pat. No. 9,944,604, which is a division of application No. 12/809,951, filed as application No. PCT/EP2008/010418 on Dec. 9, 2008, now abandoned.

(30) Foreign Application Priority Data

Dec. 21, 2007 (EP) .................... 07150343

(51) Int. Cl.
| | | |
|---|---|---|
| C07D 213/60 | (2006.01) |
| A01N 37/46 | (2006.01) |
| A01N 43/08 | (2006.01) |
| A01N 43/10 | (2006.01) |
| A01N 43/40 | (2006.01) |
| A01N 43/56 | (2006.01) |
| A01N 43/82 | (2006.01) |
| A01N 47/20 | (2006.01) |
| C07C 237/42 | (2006.01) |
| C07C 271/28 | (2006.01) |
| C07C 317/44 | (2006.01) |
| C07C 323/62 | (2006.01) |

(52) U.S. Cl.
CPC ......... *C07D 213/60* (2013.01); *A01N 37/46* (2013.01); *A01N 43/08* (2013.01); *A01N 43/10* (2013.01); *A01N 43/40* (2013.01); *A01N 43/56* (2013.01); *A01N 43/82* (2013.01); *A01N 47/20* (2013.01); *C07C 237/42* (2013.01); *C07C 271/28* (2013.01); *C07C 317/44* (2013.01); *C07C 323/62* (2013.01); *C07C 2601/10* (2017.05); *C07C 2601/16* (2017.05)

(58) Field of Classification Search
None
See application file for complete search history.

(56) References Cited

U.S. PATENT DOCUMENTS

| | | |
|---|---|---|
| 3,309,367 A | 3/1967 | Hirt |
| 6,001,879 A | 12/1999 | Seitz et al. |
| 6,794,392 B1 | 9/2004 | Suzuki et al. |
| 2007/0129407 A1* | 6/2007 | Koyanagi ............ A01N 43/56 514/341 |
| 2007/0275980 A1 | 11/2007 | Yoshida et al. |
| 2009/0099204 A1 | 4/2009 | Yoshida et al. |
| 2009/0233962 A1 | 9/2009 | Kai et al. |
| 2011/0009457 A1 | 1/2011 | Goergens et al. |

FOREIGN PATENT DOCUMENTS

| | | | |
|---|---|---|---|
| CA | 2 616 749 A1 | 2/2007 | |
| EP | 1 661 886 A | 5/2006 | |
| EP | 1 938 685 A1 | 7/2008 | |
| JP | H 11511442 A | 10/1999 | |
| JP | 2006-306771 A | 11/2005 | |
| JP | 2007099761 A | 4/2007 | |
| WO | 9708135 A1 | 3/1997 | |
| WO | 2005/021488 A1 | 3/2005 | |
| WO | 2007/013150 A1 | 2/2007 | |
| WO | 2007/013332 A1 | 2/2007 | |
| WO | 2007/017075 A1 | 2/2007 | |
| WO | WO 2007/017075 * | 2/2007 | .......... C07C 237/42 |
| WO | 2007083394 A1 | 7/2007 | |

OTHER PUBLICATIONS

Turberg Declaration Under 37 C.F.R. 1.132 submitted Mar. 7, 2017 in U.S. Appl. No. 13/456,880 (Year: 2017).*
English language Abstract of Japanese Patent Publication No. JP 2006-306771 A, European Patent Office, espacenet database—Worldwide (2005).
International Search Report of International Application No. PCT/EP2008/010418, European Patent Office, Netherlands, dated Sep. 11, 2009.

* cited by examiner

*Primary Examiner* — Craig D Ricci
(74) *Attorney, Agent, or Firm* — McBee Moore Woodward & Vanik IP, LLC

(57) ABSTRACT

The invention relates to a composition comprising at least one aminobenzamide compound or a salt thereof for controlling animal parasites, veterinary pharmaceutical compositions comprising at least one aminobenzamide of formula (I) for preventing infection with diseases transmitted through parasites, its use for the preparation of a veterinary pharmaceutical for controlling animal parasites, and a method for preventing infection with diseases transmitted through parasites.

13 Claims, No Drawings

AMINOBENZAMIDE DERIVATIVES AS USEFUL AGENTS FOR CONTROLLING ANIMAL PARASITES

CROSS-REFERENCE TO RELATED APPLICATIONS

This application is a Divisional application of U.S. patent application Ser. No. 13/456,880, filed 26 Apr. 2012, which is a Divisional application of U.S. patent application Ser. No. 12/809,951, filed 13 Sep. 2010, which is a National Stage entry of International Application No. PCT/EP2008/010418, filed 9 Dec. 2008, which claims priority to European Patent Application No. 07150343.7, filed 21 Dec. 2007. The disclosures of the priority applications are incorporated in their entirety herein by reference.

The invention relates to a composition comprising at least one aminobenzamide derivatives or a salt thereof for controlling animal parasites, veterinary pharmaceutical compositions comprising at least one aminobenzamide derivatives or a salt thereof for preventing infection with diseases transmitted through parasites, its use for the preparation of a veterinary pharmaceutical for controlling animal parasites, and a method for preventing infection with diseases transmitted through parasites.

The infestation of animals, domestic animals, companion animals and agricultural livestock alike, with parasites represents a problem. Often, the infested animals are infected with diseases transmitted through parasites, like e.g. lyme disease, a variety of sometimes fatal viral diseases or the immune system of the animals becomes weak due to the infestation, so that the animals become prone to other diseases, like e.g. bacterial infections. With the result that costly medicaments have to be administered, and, if the treated animals are agricultural livestock then the food safety is jeopardized. Additionally, the infestation of agricultural livestock with parasites is very often accompanied with a decrease in performance in terms of quality and quantity of produced meat, milk, egg, wool, or fur.

In particular, blood-sucking ectoparasites and ectoparasites causing myiasis are potential transmitters of a broad variety of pathogens besides all other secondary effects of the ectoparasitic infestation as there are blood-loss, irritation, inflammation, secondary bacterial infection, secondary parasiticidal infection (e.g. myiasis) and direct toxicosis (tick paralysis).

Although there are several compounds known to combat animal parasites there is still a need for new compounds. Especially in the field of live-stock the treated ectoparasites are often present in high numbers. Together with repeated treatments necessary to minimize damage to the host animals there is a steadily increasing risk that the ectoparasites are developing a resistance against the existing veterinary pharmaceuticals. There is also a need for veterinary pharmaceuticals which prevent the infestation of animals with parasites. And, moreover, for compounds which can prevent blood meal or lesions caused by ectoparasites and thus additionally can reduce the risk of transmitting vector-borne diseases to animals and humans.

From WO 2005/021488 A, WO 2005/073165 A, WO 2006/137376 A, WO 2006/137395 A, JP 2006/306771, WO 2007/017075 A, WO2007/013150 A and WO 2007/013332 A it is known that certain aminobenzamide derivatives can be used as insecticides in the agricultural and horticultural field.

The inventors now have found that certain aminobenzamide derivatives or compositions comprising at least one optically active aminobenzamide derivative exhibit excellent activity against animal parasites and thus can be used as veterinary pharmaceutical, especially for preventing infection with diseases which are transmitted through animal parasites.

FIRST EMBODIMENT

Therefore, in a first embodiment, the invention relates to a pharmaceutical composition comprising at least one aminobenzamide derivative of formula (I), or a salt thereof.

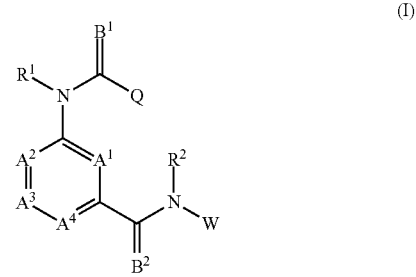

(I)

wherein
$A^1$, $A^2$, $A^3$ and $A^4$ each represent independent from each other C—X, N or N=O;
X represents independent from each other a hydrogen atom, a halogen atom, a hydroxy group, a $C_1$-$C_6$ alkyl group or a trifluoromethyl group;
$B^1$ and $B^2$ each represent independent from each other an oxygen atom or a sulfur atom;
$R^1$ and $R^2$ respectively represent independent from each other a hydrogen atom, a $C_1$-$C_6$ alkyl group, a $C_1$-$C_6$ haloalkyl group, a $C_1$-$C_6$ alkoxy group, a $C_1$-$C_6$ haloalkoxy group, a $C_1$-$C_6$ alkylthio group, a $C_1$-$C_6$ haloalkylthio group, a $C_1$-$C_6$ alkylcarbonyl group, a $C_1$-$C_6$ haloalkylcarbonyl group; or represents a phenyl group or a benzyl group optionally substituted with at least one group selected from the group consisting of $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, $C_1$-$C_6$ haloalkyl, $C_1$-$C_6$ haloalkoxy, $C_1$-$C_6$ haloalkylthio, $C_1$-$C_6$ haloalkylsulfinyl, $C_1$-$C_6$ haloalkylsulfonyl, nitro, hydroxy, and halogen; or pyridyl, pyrazolyl, thienyl, furyl, isoxazolyl, thiadiazolyl or pyridylmethyl, pyrazolylmethyl, thienylmethyl, furylmethyl, isoxazolylmethyl, or thiadiazolylmethyl optionally substituted with at least one group selected from the group consisting of $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, $C_1$-$C_6$ haloalkyl, $C_1$-$C_6$ haloalkoxy, $C_1$-$C_6$ haloalkylthio, $C_1$-$C_6$ haloalkylsulfinyl, $C_1$-$C_6$ haloalkylsulfonyl, nitro, hydroxy, and halogen;
Q represents L or Y—$R^6$
with
Y representing oxygen, suflur, amino, $C_1$-$C_4$ aminoalkyl; and
$R^6$ representing a $C_1$-$C_6$ alkyl group, a $C_1$-$C_6$ haloalkyl group, a $C_2$-$C_6$ alkenyl group, a $C_2$-$C_6$ haloalkenyl group, a $C_2$-$C_6$ alkynyl group, a $C_2$-$C_6$ haloalkynyl group, a $C_3$-$C_8$ cycloalkyl group or a $C_3$-$C_8$ halocycloalkyl group; or
-$E_1$-$Z_1$—$R^7$ (wherein $E_1$ represents a $C_1$-$C_4$ alkylene group, a $C_2$-$C_4$ alkenylene group, a $C_3$-$C_4$ alkynylene group, a $C_1$-$C_4$ haloalkylene group, a $C_2$-$C_4$ haloalkenylene group or a $C_3$-$C_4$ haloalkynylene group, $R^7$ represents a hydrogen atom, a $C_1$-$C_6$ alkyl group, a $C_2$-$C_6$ alkenyl group, a $C_2$-$C_6$ alkynyl group, a $C_1$-$C_6$ haloalkyl group, a $C_2$-$C_6$ haloalkenyl group or a $C_2$-$C_6$ haloalkynyl group, and $Z_1$ represents —O—, —S—, —SO—, —SO$_2$—, —C(=O)—, —C(=O)O—, —OC(=O)—, —N($R_8$)—, —C(=O)N($R_8$)— or —N($R_8$)C(=O)—); or -$E_2$-$R_9$ (wherein $E_2$ represents a $C_1$-$C_4$ alkylene group, a $C_2$-$C_4$ alkenylene group, a $C_2$-$C_4$ alkynylene group, a $C_1$-$C_4$ haloalkylene group, a $C_2$-$C_4$ haloalkenylene group or a $C_3$-$C_4$ haloalkynylene group; and $R_9$ represents a $C_3$-$C_8$ cycloalkyl group, a $C_3$-$C_8$ halocycloalkyl group, a cyano group, a nitro group, a hydroxy group, a phenyl group, or a substituted phenyl group having one or more substituents which may be the same or different and which are selected from a halogen atom, a $C_1$-$C_6$ alkyl group, a $C_1$-$C_6$ haloalkyl group, a $C_1$-$C_6$ alkoxy group, a $C_1$-$C_6$ haloalkoxy group, a $C_1$-$C_6$ alkylthio group, a $C_1$-$C_6$ haloalkylthio group, a $C_1$-$C_6$ alkylsulfinyl group, a $C_1$-$C_6$ haloalkylsulfinyl group, a $C_1$-$C_6$ alkylsulfonyl group, a $C_1$-$C_6$ haloalkylsulfonyl group, a cyano group, a nitro group, a hydroxy group, a $C_1$-$C_4$ alkylcarbonyl group, a $C_1$-$C_4$ haloalkylcarbonyl group, a $C_1$-$C_4$ alkylcarbonyloxy group and a $C_1$-$C_4$ alkoxycarbonyl group, or a pyridyl group, or a substituted pyridyl group having one or more substituents which are selected from a halogen atom, a $C_1$-$C_6$ haloalkyl group and a $C_1$-$C_6$ haloalkoxy group, a thienyl group or a tetrahydrofuran group);

L represents a phenyl group; or
a heterocyclyl group; or
hydrogen, a $C_1$-$C_6$ alkyl group, a $C_2$-$C_6$ alkenyl group, a $C_2$-$C_6$ alkynyl group, a $C_3$-$C_8$ cycloalkyl group, a $C_3$-$C_5$ cycloalkenyl group, a $C_1$-$C_6$ aldehyd group, a $C_1$-$C_6$ iminoaldehyd group, a $C_1$-$C_6$ alkoxyiminoaldehyd group, a $C_1$-$C_6$ alkoxyimino-$C_1$-$C_6$-alkyl group, a $C_1$-$C_6$ alkoxy group, a $C_1$-$C_6$ alkylthio group, a $C_1$-$C_6$ haloalkylthio group, a $C_1$-$C_6$ alkylsulfinyl group, and a $C_1$-$C_6$ alkylsulfonyl group;

wherein the above-mentioned residues are each optionally substituted with a halogen atom, a $C_1$-$C_4$ alkyl group, a $C_1$-$C_4$ haloalkyl group, a $C_2$-$C_4$ alkenyl group, a $C_2$-$C_4$ haloalkenyl group, a $C_2$-$C_4$ alkynyl group, a $C_2$-$C_4$ haloalkynyl group, a $C_3$-$C_6$ cycloalkyl group, a $C_3$-$C_6$ halocycloalkyl group, a $C_1$-$C_3$ alkoxy group, a $C_1$-$C_3$ haloalkoxy group, a $C_1$-$C_3$ alkylthio group, a $C_1$-$C_3$ haloalkylthio group, a $C_1$-$C_3$ alkylsulfinyl group, a $C_1$-$C_3$ haloalkylsulfinyl group, a $C_1$-$C_3$ alkylsulfonyl group, a $C_1$-$C_3$ haloalkylsulfonyl group, a $C_1$-$C_4$ alkylamino group, a di-$C_1$-$C_4$ alkylamino group, a cyano group, a nitro group, a hydroxy group, a $C_1$-$C_4$ alkylcarbonyl group, a $C_1$-$C_4$ alkylcarbonyloxy group, a $C_1$-$C_4$ alkoxycarbonyl group, an acetylamino group, a phenyl group, and a pyridyl group;

W represents a phenyl group, or a substituted phenyl group having one or more substituents which may be the same or different and which are selected from a halogen atom, a $C_1$-$C_4$ alkyl group, a $C_1$-$C_4$ haloalkyl group, $C_1$-$C_4$ haloalkyl $C_1$-$C_4$ alkoxy group, $C_1$-$C_4$ haloalkyl $C_1$-$C_4$ haloalkoxy group, a $C_1$-$C_4$ alkoxy group, a $C_1$-$C_4$ haloalkoxy group, a $C_1$-$C_3$ alkylthio group, a $C_1$-$C_3$ haloalkylthio group, a $C_1$-$C_3$ alkylsulfinyl group, a $C_1$-$C_3$ haloalkylsulfinyl group, a $C_1$-$C_3$ alkylsulfonyl group, a $C_1$-$C_3$ haloalkylsulfonyl group, a cyano group, a carbony-$C_1$-$C_4$-alkyl group, a carbony-$C_1$-$C_4$-haloalkyl group; or a $SF_5$ group;

for preventing infection with diseases transmitted through parasites.

The aminobenzamides of the formula (I) are defined preferably and most preferably by the following substituents:

$A^1$ is preferably independent from each other selected from the group consisting of C—X and N;
is more preferably C—X; and
is most preferably selected from the group consisting of CH, C-Halogen, in particular C—F, C—$CH_3$, and C—OH.

$A^2$, $A^3$ and $A^4$ are preferably independent from each other selected from the group of C—X and N;
are more preferably C—X; and
are most preferably CH.

X
is preferably selected from the group consisting of a hydrogen atom, a halogen atom, a hydroxy group, and a $C_1$-$C_6$ alkyl group;
is most preferably selected from the group consisting of a hydrogen atom, a halogen atom, a hydroxy group and a $C_1$-$C_3$ alkyl group.

$B^1$ and $B^2$ are each an oxygen atom.

$R^1$ and $R^2$ are preferably independent from each other selected from the group consisting of a hydrogen atom, a $C_1$-$C_4$ alkyl group, a $C_1$-$C_4$ haloalkyl group; a phenyl group or a benzyl group optionally substituted with at least one group selected from the group consisting of $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, $C_1$-$C_6$ haloalkyl, $C_1$-$C_6$ haloalkoxy, $C_1$-$C_6$ haloalkylthio, $C_1$—C haloalkylsulfinyl, $C_1$-$C_6$ haloalkylsulfonyl, nitro, hydroxy, and halogen; and a pyridyl group which is optionally substituted with at least one group selected from the group consisting of $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, $C_1$-$C_6$ haloalkyl, $C_1$-$C_6$ haloalkoxy, $C_1$-$C_6$ haloalkylthio, $C_1$-$C_6$ haloalkylsulfinyl, $C_1$-$C_6$ haloalkylsulfonyl, nitro, hydroxy, and halogen;
are more preferably independent from each other selected from the group consisting of hydrogen atom, a $C_1$-$C_4$ alkyl group; a benzyl group optionally substituted with at least one group selected from the group consisting of $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, $C_1$-$C_6$ haloalkyl, $C_1$-$C_6$ haloalkoxy, $C_1$-$C_6$ haloalkylthio, $C_1$-$C_6$ haloalkylsulfinyl, $C_1$-$C_6$ haloalkylsulfonyl, nitro, hydroxy, and halogen; and a pyridyl group which is optionally substituted with at least one group selected from the group consisting of $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, $C_1$-$C_6$ haloalkyl, $C_1$-$C_6$ haloalkoxy, $C_1$-$C_6$ haloalkylthio, $C_1$-$C_6$ haloalkylsulfinyl, $C_1$-$C_6$ haloalkylsulfonyl, nitro, hydroxy, and halogen; are most preferably independent from each other selected from the group consisiting of hydrogen, pyridine-3-yl-methyl, 2-fluoro-benzyl, 2-chloro-pyridin-3-yl-methyl, pyridin-2-yl-methyl and methyl.

Q preferably
represents L or Y—$R^6$
with
Y representing oxygen; and
$R^6$ representing a $C_1$-$C_6$ alkyl group, a $C_1$-$C_6$ haloalkyl group, a $C_2$-$C_6$ alkenyl group, a $C_2$-$C_6$ haloalkenyl group, a $C_2$-$C_6$ alkynyl group, a $C_2$-$C_6$ haloalkynyl group, a $C_3$-$C_5$ cycloalkyl group or a $C_3$-$C_8$ halocycloalkyl group; or
more preferably represents L or Y—$R^6$
with
Y representing oxygen; and
$R^6$ representing a $C_1$-$C_6$ alkyl group or a $C_1$-$C_6$ haloalkyl group,
most preferably represents L or Y—$R^6$
with
Y representing oxygen; and
$R^6$ representing CH, $C_2H_5$, i-$C_3H_7$, $CH_2CCl_3$, $CH(CH_2F)_2$, $(CH_2)_2Cl$ and $CH_2CF_3$.

L preferably represents a phenyl group; or a heterocyclyl group selected from the group consisting of a pyridyl group, a thiophenyl group, a furanly group, a pyrazolyl group, a thiadiazolyl group; or hydrogen, a $C_1$-$C_6$ alkyl group, a $C_2$-$C_6$ alkenyl group, a $C_2$-$C_6$ alkynyl group, a $C_3$-$C_8$ cycloalkyl group, a $C_3$-$C_8$ cycloalkenyl group, a $C_1$-$C_6$ aldehyd group, a $C_1$-$C_6$ iminoaldehyd group, a $C_1$-$C_6$ alkoxyiminoaldehyd group, a $C_1$-$C_6$ alkoxyimino-$C_1$-$C_6$-alkyl group, a $C_1$-$C_6$ alkoxy group, a $C_1$-$C_6$ alkylthio group, a $C_1$-$C_6$ alkylsulfinyl group, and a $C_1$-$C_6$ alkylsulfonyl group;

wherein the above-mentioned residues are each optionally substituted with a halogen atom, a $C_1$-$C_4$ alkyl group, a $C_1$-$C_4$ haloalkyl group, a $C_2$-$C_4$ alkenyl group, a $C_2$-$C_4$ haloalkenyl group, a $C_2$-$C_4$ alkynyl group, a $C_2$-$C_4$ haloalkynyl group, a $C_3$-$C_6$ cycloalkyl group, a $C_3$-$C_6$ halocycloalkyl group, a $C_1$-$C_3$ alkoxy group, a $C_1$-$C_3$ haloalkoxy group, a $C_1$-$C_3$ alkylthio group, a $C_1$-$C_3$ haloalkylthio group, a $C_1$-$C_3$ alkylsulfinyl group, a $C_1$-$C_3$ haloalkylsulfinyl group, a $C_1$-$C_3$ alkylsulfonyl group, a $C_1$-$C_3$ haloalkylsulfonyl group, a $C_1$-$C_4$ alkylamino group, a di-$C_1$-$C_4$ alkylamino group, a cyano group, a nitro group, a hydroxy group, a $C_1$-$C_4$ alkylcarbonyl group, a $C_1$-$C_4$ alkylcarbonyloxy group, a $C_1$-$C_4$ alkoxycarbonyl group, an acetylamino group, a phenyl group, and a pyridyl group;

more preferably represents a phenyl group; or a heterocyclyl group selected from the group consisting of a pyridyl group, a thiophenyl group, a furanly group, a pyrazolyl group, a thiadiazolyl group; or a $C_1$-$C_6$ alkyl group, a $C_2$-$C_6$ alkenyl group, a $C_2$-$C_6$ alkynyl group, a $C_3$-$C_8$ cycloalkyl group, a $C_3$-$C_8$ cycloalkenyl group, a $C_1$-$C_6$ aldehyd group, and a $C_1$-$C_6$ iminoaldehyd group, a $C_1$-$C_6$ alkoxyiminoaldehyd group, a $C_1$-$C_6$ alkoxyimino-$C_1$-$C_6$-alkyl group;

wherein the above-mentioned residues are each optionally substituted with a halogen atom, a $C_1$-$C_4$ alkyl group, a $C_1$-$C_4$ haloalkyl group, a $C_2$-$C_4$ alkenyl group, a $C_1$-$C_3$ alkoxy group, a $C_1$-$C_3$ alkylthio group, a $C_1$-$C_4$ alkylamino group, a di-$C_1$-$C_4$ alkylamino group, a cyano group, a nitro group, and a hydroxy group;

most preferably represents pyridin-2-yl, pyridin-3-yl, pyridin-4-yl, 2-fluoropyridin-3-yl, 6-fluoropyridin-3-yl, 4,6-difluoropyridin-3-yl, 2-chloropyridin-3-yl, 2-chloropyridin-4-yl, 2-chloro-pyridin-5-yl, 3-chloropyridin-2-yl, 5-chloropyridin-3-yl, 6-chloropyridin-3-yl, 3,5-dichloropyridin-2-yl, 2-bromopyridin-3-yl, 2-fluoro-pyridin-3-yl, 2-fluoro-pyridin-5-yl, 2-methylpyridin-3-yl, 4-(trifluoromethyl)pyridin-2-yl, 4-(trifluoromethyl)pyridin-3-yl, 3-chloro-5-(trifluoromethyl)pyridin-2-yl, 3-(trifluoromethyl)pyridin-2-yl, 2,6-dichloro-pyridin-3-yl, 2,6-dichloropyridin-4-yl, 3-hydroxypyridin-2-yl, 6-chloro-4-(trifluoromethyl)pyridin-3-yl, thiophen-2-yl, thiophen-3-yl, 2-chlorothiophen-3-yl, 2-chloro-thiophene-5-yl, 3-chlorothiophene-2-yl, 3-chlorothiophen-2-yl, 5-chlorothiophen-2-yl, 2,5-dichlorothiophen-3-yl, 3-methoxy-5-(trifluoromethyl)thiophen-2-yl, 3-methyl-thiophene-2-yl, furan-2-yl, furan-3-yl, 2-bromo-furan-5-y, 12,3-dibromo-furan-5-yl, 3-(tert-butyl)-1-methylpyrazol-5-yl, 5-chloro-1-methyl-3-(trifluoromethyl)pyrazole, 4-bromo-1-ethyl-3-methylpyrazol-5-yl, 4-methyl-1,2,3-thiadiazol-5-yl, phenyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 2-iodophenyl, 2,3-dichlorophenyl, 2,4-dichlorophenyl, 2,5-dichlorophenyl, 2,6-dichlorophenyl, 3,4-dichlorophenyl, 3,5-dichlorophenyl, 2-chloro-6-fluorophenyl, 2,3-difluorophenyl, 2,4-difluorophenyl, 2,5-difluorophenyl, 2,6-difluorophenyl, 2,4,6-trifluorophenyl, 2-methylphenyl, 3-methylphenyl, 4-methylphenyl, 2-ethylphenyl, 4-methylthiophenyl, 4-methoxyphenyl, 4-ethoxyphenyl, 4-(trifluoromethoxy)phenyl, 2-(trifluoromethyl)phenyl, 3-(trifluoromethyl)phenyl, 4-(trifluoromethyl)phenyl, 4-(trifluoromethylthio)phenyl, 2,4,6-trifluorophenyl, 2-nitrophenyl, 2,3-difluorophenyl, 2,4-difluorophenyl, 2,6-difluorophenyl, 4-methylsulfinylphenyl, 4-methylsulfonylphenyl, 4-(trifluoromethylsulfonyl)phenyl, 4-(trifluoromethylsulfinyl)phenyl, 2-nitrophenyl, isoxazol-5-yl, 5-methylisoxazol-4-yl, 4-cyano-phenyl, 4-nitro-phenyl, 2-chloro-4-nitro-phenyl, 2-chloro-3-amino-phenyl, (E)-propenyl, 2-chlorocyclohex-1-ene-1-yl, methylidenecyclohexane-2-yl, (Z)-2-fluorostyrene-2-yl, (E)-but-2-en-2-yl, (E)-pent-2-en-2-yl, (Z)-but-2-en-2-yl, (E)-1-chloroethene-1-yl cyclopropyl, (E)-2-methylstyrene-2-yl, cyclohexen-1-yl, cyclopenten-1-yl, 1-methoxyiminoethanal-1-yl, formyl, ethyle, propyle, isopropyle, sec.-butyle, 4-fluoro-benzyl, iso-butyle, and $Cl(CH_2)_3$.

W represents preferably a substituted phenyl group having one or more substituents which may be the same or different and which are selected from the group consisting of a halogen atom, a $C_1$-$C_4$ alkyl group, a $C_1$-$C_4$ haloalkyl group, $C_1$-$C_4$ haloalkyl $C_1$-$C_4$ alkoxy group, $C_1$-$C_4$ haloalkyl $C_1$-$C_4$ haloalkoxy group, a $C_1$-$C_4$ alkoxy group, a $C_1$-$C_4$ haloalkoxy group, a $C_1$-$C_3$ alkylthio group, a $C_1$-$C_3$ haloalkylthio group, a $C_1$-$C_3$ alkylsulfinyl group, a $C_1$-$C_3$ haloalkylsulfinyl group, a $C_1$-$C_3$ alkylsulfonyl group, a $C_1$-$C_3$ haloalkylsulfonyl group, a cyano group or a $SF_5$ group;

more preferably represents a substituted phenyl group having one or more substituents which may be the same or different and which are selected from the group consisting of a halogen atom, a $C_1$-$C_4$ alkyl group, a $C_1$-$C_4$ haloalkyl group, a $C_1$-$C_3$ alkylthio group, a $C_1$-$C_3$ haloalkylthio group, a $C_1$-$C_3$ alkylsulfinyl group, a $C_1$-$C_3$ haloalkylsulfinyl group, a $C_1$-$C_3$ alkylsulfonyl group, a $C_1$-$C_3$ haloalkylsulfonyl, a carbonyl-$C_1$-$C_4$-alkyl group, a carbonyl-$C_1$-$C_4$-haloalkyl group, and a $SF_5$ group;

most preferably

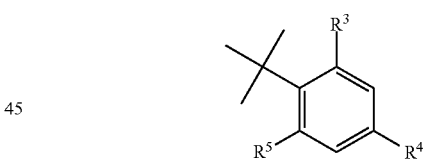

with $R^3$ being preferably selected from the group consisiting of a halogen atom, $C_1$-$C_4$ alkyl group;
being more preferably selected from the group consisiting of a halogen atom, a methyl group and an ethyl group;

$R^4$ being preferably selected from the group consisting of a $C_1$-$C_4$ haloalkyl group, a $C_1$-$C_3$ alkylthio group, a $C_1$-$C_3$ haloalkylthio group, a $C_1$-$C_3$ alkylsulfinyl group, a $C_1$-$C_3$ haloalkylsulfinyl group, a $C_1$-$C_3$ alkylsulfonyl group, a $C_1$-$C_3$ haloalkylsulfonyl, a carbonyl-$C_1$-$C_4$-alkyl group, a carbonyl-$C_1$-$C_4$-haloalkyl group, and a $SF_5$ group;

$R^4$ being more preferably selected from the group consisting of $CF_3$, $CF(CF_3)_2$, $CH(CF_3)_2$, $C_2F_5$, $SCF_3$, $SC_2F_5$, n-$SC_3F_7$, $S(O)CF_3$, $S(O)C_2F_5$, $S(O)$-n-$C_3F_7$, $SO_2CF_3$, $SO_2C_2F_5$, $SO_2$-n-$C_3F_7$, $S(O)CH_2CF_3$, Br, $SF_5$, $C(OC_2H_5)(CF_3)_2$, and $C(OCH_3)(CF_3)_2$;

$R^5$ being preferably selected from the group consisting of halogen atom, a $C_1$-$C_4$ alkyl group, and a $C_1$-$C_4$ haloalkyl group;

$R^5$ being most preferably selected from the group consisting of a halogen atom, $CH_3$, $C_2H_5$, $C_2F_5$, $CH(CH_3)_2$, $i\text{-}C_3H_7$, $n\text{-}C_3H_7$, and $SCF_3$.

SECOND EMBODIMENT

In a second embodiment, the composition as described in the first or second embodiment comprises a compound of formula (I-1) wherein

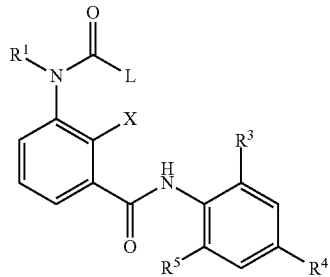

I-1

X represents a hydrogen atom, a halogen atom, a hydroxy group, a $C_1\text{-}C_6$ alkyl group or a trifluoromethyl group;
$R^1$ represents a hydrogen atom, a $C_1\text{-}C_6$ alkyl group a $C_1\text{-}C_6$ haloalkyl group, a $C_1\text{-}C_6$ alkoxy group, a $C_1\text{-}C_6$ haloalkoxy group, a $C_1\text{-}C_6$ alkylthio group, a $C_1\text{-}C_6$ haloalkylthio group, a $C_1\text{-}C_6$ alkylcarbonyl group, a $C_1\text{-}C_6$ haloalkylcarbonyl group or represents phenyl or benzyl optionally substituted with at least one group selected from the group consisting of $C_1\text{-}C_6$ alkyl, $C_1\text{-}C_6$ alkoxy, $C_1\text{-}C_6$ alkylthio, $C_1\text{-}C_6$ alkylsulfinyl, $C_1\text{-}C_6$ alkylsulfonyl, $C_1\text{-}C_6$ haloalkyl, $C_1\text{-}C_6$ haloalkoxy, $C_1\text{-}C_6$ haloalkylthio, $C_1\text{-}C_6$ haloalkylsulfinyl, $C_1\text{-}C_6$ haloalkylsulfonyl, nitro, hydroxy, and halogen; or pyridyl, pyrazolyl, thienyl, furyl, isoxazolyl, thiadiazolyl or pyridylmethyl, pyrazolylmethyl, thienylmethyl, furylmethyl, isoxazolylmethyl, or thiadiazolylmethyl optionally substituted with at least one group selected from the group consisting of $C_1\text{-}C_6$ alkyl, $C_1\text{-}C_6$ alkoxy, $C_1\text{-}C_6$ alkylthio, $C_1\text{-}C_6$ alkylsulfinyl, $C_1\text{-}C_6$ alkylsulfonyl, $C_1\text{-}C_6$ haloalkyl, $C_1\text{-}C_6$ haloalkoxy, $C_1\text{-}C_6$ haloalkylthio, $C_1\text{-}C_6$ haloalkylsulfinyl, $C_1\text{-}C_6$ haloalkylsulfonyl, nitro, hydroxy, and halogen
$R^3$ and $R^5$ represents independent from each other a halogen atom, a $C_1\text{-}C_4$ alkyl group, a $C_1\text{-}C_4$ haloalkyl group, a $C_1\text{-}C_4$ alkoxy group, a $C_1\text{-}C_4$ haloalkoxy group, $C_1\text{-}C_3$ alkylthio group, a $C_1\text{-}C_3$ haloalkylthio group, a $C_1\text{-}C_3$ alkylsulfinyl group, a $C_1\text{-}C_3$ haloalkylsulfinyl group, a $C_1\text{-}C_3$ alkylsulfonyl group, a $C_1\text{-}C_3$ haloalkylsulfonyl group or a cyano group;
$R^4$ represents $C_1\text{-}C_4$ alkyl group, a $C_1\text{-}C_4$ haloalkyl group, $C_1\text{-}C_4$ haloalkyl $C_1\text{-}C_4$ alkoxy group, $C_1\text{-}C_4$ haloalkyl $C_1\text{-}C_4$ haloalkoxy group, a $C_1\text{-}C_4$ alkoxy group, a $C_1\text{-}C_4$ haloalkoxy group, a $C_1\text{-}C_3$ alkylthio group, a $C_1\text{-}C_3$ haloalkylthio group, a $C_1\text{-}C_3$ alkylsulfinyl group, a $C_1\text{-}C_3$ haloalkylsulfinyl group, a $C_1\text{-}C_3$ alkylsulfonyl group, a $C_1\text{-}C_3$ haloalkylsulfonyl group or a $SF_5$ group;
L represents a phenyl group, or a substituted phenyl group having one or more substituents which may be the same or different and which are selected from a halogen atom, a $C_1\text{-}C_4$ alkyl group, a $C_1\text{-}C_4$ haloalkyl group, a $C_2\text{-}C_4$ alkenyl group, a $C_2\text{-}C_4$ haloalkenyl group, a $C_2\text{-}C_4$ alkynyl group, a $C_2\text{-}C_4$ haloalkynyl group, a $C_3\text{-}C_6$ cycloalkyl group, a $C_3\text{-}C_6$ halocycloalkyl group, a $C_1\text{-}C_3$ alkoxy group, a $C_1\text{-}C_3$ haloalkoxy group, a $C_1\text{-}C_3$ alkylthio group, a $C_1\text{-}C_3$ haloalkylthio group, a $C_1\text{-}C_3$ alkylsulfinyl group, a $C_1\text{-}C_3$ haloalkylsulfinyl group, a $C_1\text{-}C_3$ alkylsulfonyl group, a $C_1\text{-}C_3$ haloalkylsulfonyl group, a $C_1\text{-}C_4$ alkylamino group, a di-$C_1\text{-}C_4$ alkylamino group, a cyano group, a nitro group, a hydroxy group, a $C_1\text{-}C_4$ alkylcarbonyl group, a $C_1\text{-}C_4$ alkylcarbonyloxy group, a $C_1\text{-}C_4$ alkoxycarbonyl group, an acetylamino group and a phenyl group; or a pyridyl group; or a pyridyl group having one or more substituents which may be the same or different and which are selected from a halogen atom, a $C_1\text{-}C_4$ alkyl group, a $C_1\text{-}C_4$ haloalkyl group, a $C_2\text{-}C_4$ alkenyl group, a $C_2\text{-}C_4$ haloalkenyl group, a $C_2\text{-}C_4$ alkynyl group, a $C_2\text{-}C_4$ haloalkynyl group, a $C_3\text{-}C_6$ cycloalkyl group, a $C_3\text{-}C_6$ halocycloalkyl group, a $C_1\text{-}C_3$ alkoxy group, a $C_1\text{-}C_3$ haloalkoxy group, a $C_1\text{-}C_3$ alkylthio group, a $C_1\text{-}C_3$ haloalkylthio group, a $C_1\text{-}C_3$ alkylsulfinyl group, a $C_1\text{-}C_3$ haloalkylsulfinyl group, a $C_1\text{-}C_3$ alkylsulfonyl group, a $C_1\text{-}C_3$ haloalkylsulfonyl group, a $C_1\text{-}C_4$ alkylamino group, a di-$C_1\text{-}C_4$ alkylamino group, a cyano group, a nitro group, a hydroxy group, a $C_1\text{-}C_4$ alkylcarbonyl group, a $C_1\text{-}C_4$ alkylcarbonyloxy group, a $C_1\text{-}C_4$ alkoxycarbonyl group, an acetylamino group and a phenyl group; or
hydrogen, a $C_1\text{-}C_4$ alkyl group, a $C_1\text{-}C_4$ haloalkyl group, a $C_2\text{-}C_4$ alkenyl group, a $C_2\text{-}C_4$ haloalkenyl group, a $C_2\text{-}C_4$ alkynyl group, a $C_2\text{-}C_4$ haloalkynyl group, a $C_3\text{-}C_6$ cycloalkyl group, a $C_3\text{-}C_6$ halocycloalkyl group, a $C_1\text{-}C_3$ alkoxy group, a $C_1\text{-}C_3$ haloalkoxy group, a $C_1\text{-}C_3$ alkylthio group, a $C_1\text{-}C_3$ haloalkylthio group, a $C_1\text{-}C_3$ alkylsulfinyl group, a $C_1\text{-}C_3$ haloalkylsulfinyl group, a $C_1\text{-}C_3$ alkylsulfonyl group and a $C_1\text{-}C_3$ haloalkylsulfonyl group; or
a $C_1\text{-}C_4$ alkyl group, a $C_1\text{-}C_4$ haloalkyl group, a $C_2\text{-}C_4$ alkenyl group, a $C_2\text{-}C_4$ haloalkenyl group, a $C_2\text{-}C_4$ alkynyl group, a $C_2\text{-}C_4$ haloalkynyl group, a $C_3\text{-}C_6$ cycloalkyl group, a $C_3\text{-}C_6$ halocycloalkyl group, a $C_1\text{-}C_3$ alkoxy group, a $C_1\text{-}C_3$ haloalkoxy group, a $C_1\text{-}C_3$ alkylthio group, a $C_1\text{-}C_3$ haloalkylthio group, a $C_1\text{-}C_3$ alkylsulfinyl group, a $C_1\text{-}C_3$ haloalkylsulfinyl group, a $C_1\text{-}C_3$ alkylsulfonyl group and a $C_1\text{-}C_3$ haloalkylsulfonyl group, each substituted with phenyl group having one or more substituents which may be the same or different and which are selected from a halogen atom, a $C_1\text{-}C_4$ alkyl group, a $C_1\text{-}C_4$ haloalkyl group, a $C_2\text{-}C_4$ alkenyl group, a $C_2\text{-}C_4$ haloalkenyl group, a $C_2\text{-}C_4$ alkynyl group, a $C_2\text{-}C_4$ haloalkynyl group, a $C_3\text{-}C_6$ cycloalkyl group, a $C_3\text{-}C_6$ halocycloalkyl group, a $C_1\text{-}C_3$ alkoxy group, a $C_1\text{-}C_3$ haloalkoxy group, a $C_1\text{-}C_3$ alkylthio group, a $C_1\text{-}C_3$ haloalkylthio group, a $C_1\text{-}C_3$ alkylsulfinyl group, a $C_1\text{-}C_3$ haloalkylsulfinyl group, a $C_1\text{-}C_3$ alkylsulfonyl group, a $C_1\text{-}C_3$ haloalkylsulfonyl group, a $C_1\text{-}C_4$ alkylamino group, a di-$C_1\text{-}C_4$ alkylamino group, a cyano group, a nitro group, a hydroxy group, a $C_1\text{-}C_4$ alkylcarbonyl group, a $C_1\text{-}C_4$ alkylcarbonyloxy group, a $C_1\text{-}C_4$ alkoxycarbonyl group, an acetylamino group and a phenyl group; or a pyridyl group;
for preventing infection with diseases transmitted through parasites.

The aminobenzamides of the formula (I-1) are defined preferably and most preferably by the following substituents:
X is preferably selected from the group consisting of a hydrogen atom, a halogen atom, a hydroxy group, and a $C_1\text{-}C_6$ alkyl group;

is most preferably selected from the group consisting of a hydrogen atom, a halogen atom, a hydroxy group and a $C_1$-$C_3$ alkyl group.

$R^1$ is preferably independent from each other selected from the group consisting of a hydrogen atom, a $C_1$-$C_4$ alkyl group, a $C_1$-$C_4$ haloalkyl group; a phenyl group or a benzyl group optionally substituted with at least one group selected from the group consisting of $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, $C_1$-$C_6$ haloalkyl, $C_1$-$C_6$ haloalkoxy, $C_1$-$C_6$ haloalkylthio, $C_1$-$C_6$ haloalkylsulfinyl, $C_1$-$C_6$ haloalkylsulfonyl, nitro, hydroxy, and halogen; and a pyridyl group which is optionally substituted with at least one group selected from the group consisting of $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, $C_1$-$C_6$ haloalkyl, $C_1$-$C_6$ haloalkoxy, $C_1$-$C_6$ haloalkylthio, $C_1$-$C_6$ haloalkylsulfinyl, $C_1$-$C_6$ haloalkylsulfonyl, nitro, hydroxy, and halogen;

is more preferably independent from each other selected from the group consisting of hydrogen atom, a $C_1$-$C_4$ alkyl group; a benzyl group optionally substituted with at least one group selected from the group consisting of $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, $C_1$-$C_6$ haloalkyl, $C_1$-$C_6$ haloalkoxy, $C_1$-$C_6$ haloalkylthio, $C_1$-$C_6$ haloalkylsulfinyl, $C_1$-$C_6$ haloalkylsulfonyl, nitro, hydroxy, and halogen; and a pyridyl group which is optionally substituted with at least one group selected from the group consisting of $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, $C_1$-$C_6$ haloalkyl, $C_1$-$C_6$ haloalkoxy, $C_1$-$C_6$ haloalkylthio, $C_1$-$C_6$ haloalkylsulfinyl, $C_1$-$C_6$ haloalkylsulfonyl, nitro, hydroxy, and halogen;

is most preferably independent from each other selected from the group consisiting of hydrogen, pyridine-3-yl-methyl, 2-fluoro-benzyl, 2-chloro-pyridin-3-yl-methyl, pyridin-2-yl-methyl and methyl.

$R^3$ being preferably selected from the group consisiting of a halogen atom, $C_1$-$C_4$ alkyl group;
being more preferably selected from the group consisiting of a halogen atom, a methyl group and an ethyl group;

$R^4$ being preferably selected from the group consisting of a $C_1$-$C_4$ haloalkyl group, a $C_1$-$C_3$ alkylthio group, a $C_1$-$C_3$ haloalkylthio group, a $C_1$-$C_3$ alkylsulfinyl group, a $C_1$-$C_3$ haloalkylsulfinyl group, a $C_1$-$C_3$ alkylsulfonyl group, a $C_1$-$C_3$ haloalkylsulfonyl, a carbonyl-$C_1$-$C_4$-alkyl group, a carbonyl-$C_1$-$C_4$-haloalkyl group, and a $SF_5$ group;
being more preferably selected from the group consisting of $CF_3$, $CF(CF_3)_2$, $CH(CF_3)_2$, $C_2F_5$, $SCF_3$, $SC_2F_5$, n-$SC_3F_7$, $S(O)CF_3$, $S(O)C_2F_5$, $S(O)$-n-$C_3F_7$, $SO_2CF_3$, $SO_2C_2F_5$, $SO_2$-n-$C_3F_7$, $S(O)CH_2CF_3$, Br, $SF_5$, $C(OC_2H_5)(CF_3)_2$, and $C(OCH_3)(CF_3)_2$;

$R^5$ being preferably selected from the group consisting of halogen atom, a $C_1$-$C_4$ alkyl group, and a $C_1$-$C_4$ haloalkyl group;
being most preferably selected from the group consisting of a halogen atom, $CH_3$, $C_2H_5$, $C_2F_5$, $CH(CH_3)_2$, i-$C_3H_7$, n-$C_3H_7$, and $SCF_3$.

L preferably represents a phenyl group; or
a heterocyclyl group selected from the group consisting of a pyridyl group, a thiophenyl group, a furanly group, a pyrazolyl group, a thiadiazolyl group; or
hydrogen, a $C_1$-$C_6$ alkyl group, a $C_2$-$C_6$ alkenyl group, a $C_2$-$C_6$ alkynyl group, a $C_3$-$C_8$ cycloalkyl group, a $C_3$-$C_8$ cycloalkenyl group, a $C_1$-$C_6$ aldehyd group, a $C_1$-$C_6$ iminoaldehyd group, a $C_1$-$C_6$ alkoxy group, a $C_1$-$C_6$ alkylthio group, a $C_1$-$C_6$ alkylsulfinyl group, and a $C_1$-$C_6$ alkylsulfonyl group;
wherein the above-mentioned residues are each optionally substituted with a halogen atom, a $C_1$-$C_4$ alkyl group, a $C_1$-$C_4$ haloalkyl group, a $C_2$-$C_4$ alkenyl group, a $C_2$-$C_4$ haloalkenyl group, a $C_2$-$C_4$ alkynyl group, a $C_2$-$C_4$ haloalkynyl group, a $C_3$-$C_6$ cycloalkyl group, a $C_3$-$C_6$ halocycloalkyl group, a $C_1$-$C_3$ alkoxy group, a $C_1$-$C_3$ haloalkoxy group, a $C_1$-$C_3$ alkylthio group, a $C_1$-$C_3$ haloalkylthio group, a $C_1$-$C_3$ alkylsulfinyl group, a $C_1$-$C_3$ haloalkylsulfinyl group, a $C_1$-$C_3$ alkylsulfonyl group, a $C_1$-$C_3$ haloalkylsulfonyl group, a $C_1$-$C_4$ alkylamino group, a di-$C_1$-$C_4$ alkylamino group, a cyano group, a nitro group, a hydroxy group, a $C_1$-$C_4$ alkylcarbonyl group, a $C_1$-$C_4$ alkylcarbonyloxy group, a $C_1$-$C_4$ alkoxycarbonyl group, an acetylamino group, a phenyl group, and a pyridyl group;
more preferably represents a phenyl group; or
a heterocyclyl group selected from the group consisting of a pyridyl group, a thiophenyl group, a furanly group, a pyrazolyl group, a thiadiazolyl group; or
a $C_1$-$C_6$ alkyl group, a $C_2$-$C_6$ alkenyl group, a $C_2$-$C_6$ alkynyl group, a $C_3$-$C_8$ cycloalkyl group, a $C_3$-$C_8$ cycloalkenyl group, a $C_1$-$C_6$ aldehyd group, and a $C_1$-$C_6$ iminoaldehyd group;
wherein the above-mentioned residues are each optionally substituted with a halogen atom, a $C_1$-$C_4$ alkyl group, a $C_1$-$C_4$ haloalkyl group, a $C_2$-$C_4$ alkenyl group, a $C_1$-$C_3$ alkoxy group, a $C_1$-$C_3$ alkylthio group, a $C_1$-$C_4$ alkylamino group, a di-$C_1$-$C_4$ alkylamino group, a cyano group, a nitro group, and a hydroxy group;
most preferably represents pyridin-2-yl, pyridin-3-yl, pyridin-4-yl, 2-fluoropyridin-3-yl, 6-fluoropyridin-3-yl, 4,6-difluoropyridin-3-yl, 2-chloropyridin-3-yl, 2-chloropyridin-4-yl, 2-chloro-pyridin-5-yl, 3-chloropyridin-2-yl, 5-chloropyridin-3-yl, 6-chloropyridin-3-yl, 3,5-dichloro-pyridin-2-yl, 2-bromopyridin-3-yl, 2-fluoro-pyridin-3-yl, 2-fluoro-pyridin-5-yl, 2-methylpyridin-3-yl, 4-(trifluoromethyl)pyridin-2-yl, 4-(trifluoromethyl)pyridin-3-yl, 3-chloro-5-(trifluoromethyl)pyridin-2-yl, 3-(trifluoromethyl)pyridin-2-yl, 2,6-dichloro-pyridin-3-yl, 2,6-dichloro-pyridin-4-yl, 3-hydroxypyridin-2-yl, 6-chloro-4-(trifluoromethyl)pyridin-3-yl, thiophen-2-yl, thiophen-3-yl, 2-chlorothiophen-3-yl, 2-chloro-thiophene-5-yl, 3-chloro-thiophene-2-yl, 3-chlorothiophen-2-yl, 5-chlorothiophen-2-yl, 2,5-dichlorothiophen-3-yl, 3-methoxy-5-(trifluoromethyl)thiophen-2-yl, 3-methyl-thiophene-2-yl, furan-2-yl, furan-3-yl, 2-bromo-furan-5-yl, 2,3-dibromo-furan-5-yl, 3-(tert-butyl)-1-methylpyrazol-5-yl, 5-chloro-1-methyl-3-(trifluoromethyl)pyrazole, 4-bromo-1-ethyl-3-methylpyrazol-5-yl, 4-methyl-1,2,3-thiadiazol-5-yl, phenyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 2-iodophenyl, 2,3-dichlorophenyl, 2,4-dichlorophenyl, 2,5-dichlorophenyl, 2,6-dichlorophenyl, 3,4-dichlorophenyl, 3,5-dichlorophenyl, 2-chloro-6-fluorophenyl, 2,3-difluorophenyl, 2,4-difluorophenyl, 2,5-difluorophenyl, 2,6-difluorophenyl, 2,4,6-trifluorophenyl, 2-methylphenyl, 3-methylphenyl, 4-methylphenyl, 2-ethylphenyl, 4-methylthiophenyl, 4-methoxyphenyl, 4-ethoxyphenyl, 4-(trifluoromethoxy)phenyl, 2-(trifluoromethyl)phenyl, 3-(trifluoromethyl)phenyl, 4-(trifluoromethyl)phenyl, 4-(trifluoromethylthio)phenyl, 2,4,6-trifluorophenyl, 2-nitrophenyl, 2,3-difluorophenyl, 2,4-difluorophenyl, 2,6-difluorophenyl, 4-methylsulfinylphenyl, 4-methylsulfonylphenyl, 4-(trifluoromethylsulfonyl)phenyl, 4-(trifluoromethylsulfinyl)phenyl, 2-nitrophenyl, isoxazol-5-yl, 5-methylisoxazol-4-yl, 4-cyano-phenyl, 4-nitro-phenyl, 2-chloro-4-nitro-phenyl, 2-chloro-3-amino-phenyl, (E)-propenyl, 2-chlorocyclohex-1-ene-1-yl, methylidenecyclohexane-2-yl, (Z)-2-fluorostyrene-2-yl, (E)-but-2-en-2-yl, (E)-pent-2-en-2-yl, (Z)-but-2-en-2-yl, (E)-1-chloroethene-1-yl cyclopropyl, (E)-2-methylstyrene-2-yl, cyclohexen-1-yl, cyclopenten-1-yl, 1-methoxyimino-ethanal-1-yl, formyl, ethyle, propyle, isopropyle, sec.-butyle 4-fluoro-benzyl, iso-butyle, and $C_1(CH_2)_3$.

THIRD EMBODIMENT

In a third embodiment the composition as described in the first or second embodiment comprises at least one compound of formula (I-2), wherein

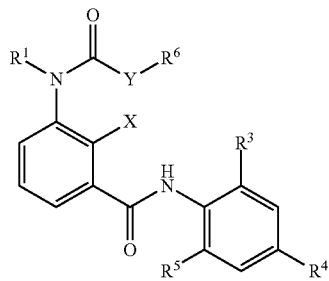

I-2

X represents a hydrogen atom, a halogen atom, a hydroxy group, a $C_1$-$C_3$ alkyl group or a trifluoromethyl group;
Y represents oxygen, suflur, amino, $C_1$-$C_4$ aminoalkyl;
$R^1$ represents a hydrogen atom, a $C_1$-$C_6$ alkyl group, a $C_1$-$C_6$ haloalkyl group, a $C_1$-$C_6$ alkoxy group, a $C_1$-$C_6$ haloalkoxy group, a $C_1$-$C_6$ alkylthio group, a $C_1$-$C_6$ haloalkylthio group, a $C_1$-$C_6$ alkylcarbonyl group, a $C_1$-$C_6$ haloalkylcarbonyl group; or represents a phenyl group or a benzyl group optionally substituted with at least one group selected from the group consisting of $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, $C_1$-$C_6$ haloalkyl, $C_1$-$C_6$ haloalkoxy, $C_1$-$C_6$ haloalkylthio, $C_1$-$C_5$ haloalkylsulfinyl, $C_1$-$C_6$ haloalkylsulfonyl, nitro, hydroxy, and halogen; or pyridyl, pyrazolyl, thienyl, furyl, isoxazolyl, thiadiazolyl or pyridylmethyl, pyrazolylmethyl, thienylmethyl, furylmethyl, isoxazolylmethyl, or thiadiazolylmethyl optionally substituted with at least one group selected from the group consisting of $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, $C_1$-$C_6$ haloalkyl, $C_1$-$C_6$ haloalkoxy, $C_1$-$C_6$ haloalkylthio, $C_1$-$C_6$ haloalkylsulfinyl, $C_1$-$C_6$ haloalkylsulfonyl, nitro, hydroxy, and halogen;
$R^3$ and $R^5$ represents independent from each other a halogen atom, a $C_1$-$C_4$ alkyl group, a $C_1$-$C_4$ haloalkyl group, a $C_1$-$C_4$ alkoxy group, a $C_1$-$C_4$ haloalkoxy group, $C_1$-$C_3$ alkylthio group, a $C_1$-$C_3$ haloalkylthio group, a $C_1$-$C_3$ alkylsulfinyl group, a $C_1$-$C_3$ haloalkylsulfinyl group, a $C_1$-$C_3$ alkylsulfonyl group, a $C_1$-$C_3$ haloalkylsulfonyl group or a cyano group;
$R^4$ represents $C_1$-$C_4$ alkyl group, a $C_1$-$C_4$ haloalkyl group, $C_1$-$C_4$ haloalkyl $C_1$-$C_4$ alkoxy group, $C_1$-$C_4$ haloalkyl $C_1$-$C_4$ haloalkoxy group, a $C_1$-$C_4$ alkoxy group, a $C_1$-$C_4$ haloalkoxy group, a $C_1$-$C_3$ alkylthio group, a $C_1$-$C_3$ haloalkylthio group, a $C_1$-$C_3$ alkylsulfinyl group, a $C_1$-$C_3$ haloalkylsulfinyl group, a $C_1$-$C_3$ alkylsulfonyl group, a $C_1$-$C_3$ haloalkylsulfonyl group or a $SF_5$ group;

$R^6$ representing a $C_1$-$C_6$ alkyl group, a $C_1$-$C_6$ haloalkyl group, a $C_2$-$C_6$ alkenyl group, a $C_2$-$C_6$ haloalkenyl group, a $C_2$-$C_6$ alkynyl group, a $C_2$-$C_6$ haloalkynyl group, a $C_3$-$C_8$ cycloalkyl group or a $C_3$-$C_8$ halocycloalkyl group; or
-$E_1$-$Z_1$—$R^7$ (wherein $E_1$ represents a $C_1$-$C_4$ alkylene group, a $C_2$-$C_4$ alkenylene group, a $C_3$-$C_4$ alkynylene group, a $C_1$-$C_4$ haloalkylene group, a $C_2$-$C_4$ haloalkenylene group or a $C_3$-$C_4$ haloalkynylene group, $R^7$ represents a hydrogen atom, a $C_1$-$C_6$ alkyl group, a $C_2$-$C_6$ alkenyl group, a $C_2$-$C_6$ alkynyl group, a $C_1$-$C_6$ haloalkyl group, a $C_2$-$C_6$ haloalkenyl group or a $C_2$-$C_6$ haloalkynyl group, and $Z_1$ represents —O—, —S—, —SO—, —$SO_2$—, —C(=O)—, —C(=O)O—, —OC(=O)—, —N($R_8$)—, —C(=O)N($R_8$)— or —N($R_8$)C(=O)—); or
-$E_2$-$R_9$ (wherein $E_2$ represents a $C_1$-$C_4$ alkylene group, a $C_2$-$C_4$ alkenylene group, a $C_3$-$C_4$ alkynylene group, a $C_1$-$C_4$ haloalkylene group, a $C_2$-$C_4$ haloalkenylene group or a $C_3$-$C_4$ haloalkynylene group; and $R_9$ represents a $C_3$-$C_8$ cycloalkyl group, a $C_3$-$C_8$ halocycloalkyl group, a cyano group, a nitro group, a hydroxy group, a phenyl group, or a substituted phenyl group having one or more substituents which may be the same or different and which are selected from a halogen atom, a $C_1$-$C_6$ alkyl group, a $C_1$-$C_6$ haloalkyl group, a $C_1$-$C_6$ alkoxy group, a $C_1$-$C_6$ haloalkoxy group, a $C_1$-$C_6$ alkylthio group, a $C_1$-$C_6$ haloalkylthio group, a $C_1$-$C_6$ alkylsulfinyl group, a $C_1$-$C_6$ haloalkylsulfinyl group, a $C_1$-$C_6$ alkylsulfonyl group, a $C_1$-$C_6$ haloalkylsulfonyl group, a cyano group, a nitro group, a hydroxy group, a $C_1$-$C_4$ alkylcarbonyl group, a $C_1$-$C_4$ haloalkylcarbonyl group, a $C_1$-$C_4$ alkylcarbonyloxy group and a $C_1$-$C_4$ alkoxycarbonyl group, or a pyridyl group, or a substituted pyridyl group having one or more substituents which are selected from a halogen atom, a $C_1$-$C_6$ haloalkyl group and a $C_1$-$C_6$ haloalkoxy group, a thienyl group or a tetrahydrofuran group);
for preventing infection with diseases transmitted through parasites.

The aminobenzamides of the formula (I) are defined preferably and most preferably by the following substituents:

X is preferably selected from the group consisting of a hydrogen atom, a halogen atom, a hydroxy group, and a $C_1$-$C_6$ alkyl group;
  is most preferably selected from the group consisting of a hydrogen atom, a halogen atom, a hydroxy group and a $C_1$-$C_3$ alkyl group.
$R^1$ is preferably independent from each other selected from the group consisting of a hydrogen atom, a $C_1$-$C_4$ alkyl group, a $C_1$-$C_4$ haloalkyl group; a phenyl group or a benzyl group optionally substituted with at least one group selected from the group consisting of $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, $C_1$-$C_6$ haloalkyl, $C_1$-$C_6$ haloalkoxy, $C_1$-$C_6$ haloalkylthio, $C_1$-$C_6$ haloalkylsulfinyl, $C_1$-$C_6$ haloalkylsulfonyl, nitro, hydroxy, and halogen; and a pyridyl group which is optionally substituted with at least one group selected from the group consisting of $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, $C_1$-$C_6$ haloalkyl, $C_1$-$C_6$ haloalkoxy, $C_1$-$C_6$ haloalkylthio, $C_1$-$C_6$ haloalkylsulfinyl, $C_1$-$C_6$ haloalkylsulfonyl, nitro, hydroxy, and halogen;
  is more preferably independent from each other selected from the group consisting of hydrogen atom, a $C_1$-$C_4$ alkyl group; a benzyl group optionally substituted with at least one group selected from the group consisting of $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, $C_1$-$C_6$ haloalkyl, $C_1$-$C_6$ haloalkoxy, $C_1$-$C_6$ haloalkylthio, $C_1$-$C_6$ haloalkylsulfinyl, $C_1$-$C_6$ haloalkylsulfonyl, nitro, hydroxy, and halogen; and a pyridyl group which is optionally substituted with at least one group selected from the group consisting of $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, $C_1$-$C_6$ haloalkyl, $C_1$-$C_6$ haloalkoxy, $C_1$-$C_6$ haloalkylthio, $C_1$-$C_6$ haloalkylsulfinyl, $C_1$-$C_6$ haloalkylsulfonyl, nitro, hydroxy, and halogen; is most preferably independent from each other selected from the group consisiting of hydrogen, pyridine-3-yl-methyl, 2-fluoro-benzyl, 2-chloro-pyridin-3-yl-methyl, pyridin-2-yl-methyl and methyl.

Y is preferably oxygen;

$R^6$ is preferably a $C_1$-$C_6$ alkyl group, a $C_1$-$C_6$ haloalkyl group, a $C_2$-$C_6$ alkenyl group, a $C_2$-$C_6$ haloalkenyl group, a $C_2$-$C_6$ alkynyl group, a $C_2$-$C_6$ haloalkynyl group, a $C_3$-$C_8$ cycloalkyl group or a $C_3$-$C_8$ halocycloalkyl group; or is more preferably a $C_1$-$C_6$ alkyl group or a $C_1$-$C_6$ haloalkyl group, is most preferably $CH_3$, $C_2H_5$, i-$C_3H_7$, $CH_2CCl_3$, $CH(CH_2F)_2$, $(CH_2)_2Cl$ or $CH_2CF_3$.

$R^3$ is preferably selected from the group consisting of a halogen atom, $C_1$-$C_4$ alkyl group;

is more preferably selected from the group consisiting of a halogen atom, a methyl group and an ethyl group;

$R^4$ is preferably selected from the group consisting of a $C_1$-$C_4$ haloalkyl group, a $C_1$-$C_3$ alkylthio group, a $C_1$-$C_3$ haloalkylthio group, a $C_1$-$C_3$ alkylsulfinyl group, a $C_1$-$C_3$ haloalkylsulfinyl group, a $C_1$-$C_3$ alkylsulfonyl group, a $C_1$-$C_3$ haloalkylsulfonyl, a carbonyl-$C_1$-$C_4$-alkyl group, a carbonyl-$C_1$-$C_4$-haloalkyl group, and a $SF_5$ group;

is more preferably selected from the group consisting of $CF_3$, $CF(CF_3)_2$, $CH(CF_3)_2$, $C_2F_5$, $SCF_3$, $SC_2F_5$, n-$SC_3F_7$, $S(O)CF_3$, $S(O)C_2F_5$, $S(O)$-n-$C_3F_7$, $SO_2CF_3$, $SO_2C_2F_5$, $SO_2$-n-$C_3F_7$, $S(O)CH_2CF_3$, Br, $SF_5$, $C(OC_2H_5)(CF_3)_2$, and $C(OCH_3)(CF_3)_2$;

$R^5$ is preferably selected from the group consisting of halogen atom, a $C_1$-$C_4$ alkyl group, and a $C_1$-$C_4$ haloalkyl group;

is most preferably selected from the group consisting of a halogen atom, $CH_3$, $C_2H$—, $C_2F_5$, $CH(CH_3)_2$, i-$C_3H_7$, n-$C_3H_7$, and $SCF_3$.

The above-mentioned compounds according to formulas (I), (I-1) and (I-2) are known from WO 2005/021488 A, WO 2005/073165 A, WO 2006/137376 A, WO 2006/137395 A, JP 2006/306771, WO 2007/017075 A, WO2007/013150 A and WO 2007/013332 A and can be synthesized according to the methods described therein.

The pharmaceutical composition comprising the above-mentioned compounds of the formulas (I), (I-1) and (I-2) is preferably a veterinary pharmaceutical composition.

The present invention further relates to the use of the aminobenzamide derivative as described in any of the first to third embodiment for controlling parasites, preferably animal parasites, most preferred ectoparasites. Ectoparasites are in particular arthropods. Most preferred groups of arthropods are acari and insects. Surprisingly it was found that the compounds have particular high activity against acari, in particular ticks and mites.

The present invention further relates to the use of a composition comprising at least one aminobenzamide derivative as described in any of the first to third embodiment for controlling parasites, preferably animal parasites, such as arthropods. Arthropods include acari, in particular ticks including hard ticks and soft ticks, mites including scab mites, ear mites, bird mites, harvest mites; arthropods also include insects like flies, lice and fleas in particular fleas for various hosts (e.g. cat fleas, dog fleas etc.), stinging flies, licking flies, parasitic fly larvae, biting lice and sucking lice.

The present invention further relates to a method for preventing infection with diseases transmitted through parasites, characterized in that a composition comprising at least one aminobenzamide derivative as described in any of the first to third embodiment is administered to the animal enterally, such as orally, topically or parenterally, such as per injection. The preferred route of administration is externally.

Moreover, it has been found that the compounds of the present invention provide excellent activity against animal parasites, particularly against arthropods attacking and/or infesting companion animals or agricultural livestock. Thus, the compounds and compositions of the invention can be used to control arthropods attacking and/or infesting companion animals and agricultural livestock.

The composition according to the invention optionally comprises further active ingredients and/or auxiliary agents, such as for example developers, surfactants, emulsifiers, solvents, foam formers or anti-foaming agents and fillers.

Examples of further active ingredients which can be used in the present invention are insecticides, bactericides, acaricides, nematicides, fungicides. Examples of such active ingredients include organic phosphorous agents, carbonate agents, chemicals of the carboxylate type, chemicals of the chlorinated hydrocarbon type and materials produced from microorganisms.

Other examples of such active ingredients include, but are not limited to, Acctylcholinesterase (AChE) inhibitors, like carbamates, such as for example alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulfan, cloethocarb, dimetilan, ethiofencarb, fenobucarb, fcnothiocarb, formetanate, furathiocarb, isoprocarb, metam-sodium, methiocarb, methomyl, metolcarb, oxamyl, pirimicarb, promecarb, propoxur, thiodicarb, thiofanox, trimethacarb, XMC, xylylcarb, and triazamate; organophosphates, such as for example acephate, azamethiphos, azinphos (-methyl, -ethyl), aromophos-ethyl, aromfenvinfos (-methyl), autathiofos, cadusafos, carbophenothion, chlorethoxyfos, chlorfenvinphos, chlormephos, chlorpyrifos (-methyl/-ethyl), coumaphos, cyanofenphos, cyanophos, chlorfenvinphos, demeton-S-methyl, demeton-S-methylsulphone, dialifos, diazinone, dichlofenthione, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidone, phosphocarb, Phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion.

Sodium channel modulators/voltage-dependent sodium channel blockers like pyrethroids, such as for example acrinathrin, allethrin (d-cis-trans, d-trans), beta-cyfluthrin, bifenthrin, bioallethrin, bioallethrin-S-cyclopentyl-isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cypermethrin (alpha-, beta-, theta-, zeta), cyphenothrin, deltamethrin, empenthrin ($_1$R-isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R-trans isomer), prallethrin, profluthrin, protrifenbute, pyresmethrin, resmethrin, RU 15525, silafluofen, tau-fluvalinate, tefluthrin, terallethrin, tetramethrin (-1R-isomer), tralomethrin, transfluthrin, ZXI 8901, pyrethrins (pyrethrum); DDT; oxadiazines, such as for example indoxacarb.

Acetylcholine receptor agonists/antagonists, like chloronicotinyls, such as for example acetamiprid, clothianidin, dinotefuran, imidacloprid, nitenpyram, nithiazine, thiacloprid, thiamethoxam, nicotine, bensultap, cartap.

Acetylcholine receptor modulators, like Spinosynes, such as for example spinosad.

GABA controlled chloride channel antagonists, like Organochlorine, such as for example camphechlor, chlordane, endosulfan, gamma-HCH, HCH, heptachlor, lindane, methoxychlor; Fiproles, such as for example acetoprole, ethiprole, fipronil, pyrafluprole, pyriprole, and vaniliprole.

Chloride channel activators, like Mectins, such as for example avermectin, emamectin, emamectin benzoate, ivermectin, milbemycin, latidectin, lepimectin, selamectin, doramectin, eprinomectin, and moxidectin.

Juvenile hormone mimetics, like for example diofenolan, epofenonane, fenoxycarb, hydroprene, kinoprene, methoprene, pyriproxifen, and triprene.

Latrophilin receptor agonists, like depsipeptides, referably cyclic depsipetides, in particular 24-membered cyclic depsipeptides, for example emodepside.

Ecdysone agonists/disruptors, like diacylhydrazines, such as for example chromafenozide, halofenozide, methoxyfenozide, tebufenozide.

Inhibitors of chitin biosynthesis, like Benzoylureas, such as for example bistrifluron, chlofluazuron, diflubenzuron, fluazuron, flucycloxuron, flufenoxuron, hexaflumuron, lufenuron, novaluron, noviflumuron, penfluron, teflubenzuron, triflumuron; buprofezin; cyromazine.

Inhibitors of oxidative phosphorylation, ATP disruptors such as diafenthiuron; organotin compounds, such as for example azocyclotin, cyhexatin, fenbutatin-oxide.

Decouplers of oxidative phosphorylation by interruption of H-proton gradients like pyrrole, such as for example chlorfenapyr; dinitrophenols, such as for example binapacyrl, dinobuton, dinocap, DNOC.

Site I electron transport inhibitors, like METI's, such as for example fenazaquin, fenpyroximate, pyrimidifen, pyridaben, tebufenpyrad, tolfenpyrad; hydramethylnon; dicofol.

Site II electron transport inhibitors, like rotenones.

Site III electron transport inhibitors, like acequinocyl, fluacrypyrim.

Microbial disruptors of insect intestinal membrane such *Bacillus thuringiensis* strains.

Inhibitors of fat synthesis, like tetronic acids, such as for example spirodiclofen, spiromesifen; tetramic acids, such as for example spirotetramat (CAS-Reg.-No.: 203313-25-1) and 3-(2,5-dimethylphenyl)-8-methoxy-2-oxo-1-azaspiro[4.5]dec-3-en-4-yl ethyl carbonate (alias: carbonic acid, 3-(2,5-dimethylphenyl)-8-methoxy-2-oxo-1-azaspiro[4.5]dec-3-en-4-yl ethyl ester, CAS-Reg.-No.: 382608-10-8); carboxamides, such as for example flonicamid.

Octopaminergic agonists, such as for example amitraz.

Inhibitor of magnesium-stimulated ATPase, like propargite benzoic acid dicarboxamides, such as for example flubendiamide; Nereistoxin analogous, such as for example thiocyclam hydrogen oxalate, thiosultap-sodium.

Biologicals, hormones or pheromones like azadirachtin, *Bacillus* spec., *Beauveria* spec., codlemone, *Metarrhizium* spec., *Paecilomyces* spec., thuringiensin, *Verticillium* spec.

Active ingredients with unknown or non-specific mode of action, like fumigants, such as for example aluminium phosphide, methyl bromide, sulphuryl fluoride; feeding inhibitors, such as for example cryolite, flonicamid, pymetrozine; mite growth inhibitors, such as for example clofentezine, etoxazole, hexythiazox; amidoflumet, benclothiaz, benzoximate, bifenazate, bromopropylate, buprofezin, quinomethionate, chlordimeform, chlorobenzilate, chloropicrin, clothiazoben, cycloprene, cyflumetofen, dicyclanil, fenoxacrim, fentrifanil, flubenzimine, flufenerim, flutenzin, gossyplure, hydramethylnone, japonilure, mctoxadiazone, petroleum, piperonyl butoxide, potassium oleate, pyridalyl, sulfluramid, tetradifon, tetrasul, triarathene, and verbutin.

Examples for parasites against which the compounds or compositions of the invention can be used include, but are not limited to, the above mentioned and, endoparasites, like for example helminths nematodes, trematodes, cestodes, for example such as Acanthocephala, Ascariasis, Cestoda, *Clonorchis sinensis*, Dracunculiasis, *Enterobius vermicularis*, Filariasis, Hookworm, *Loa loa*, Onchocerciasis, Schistosomiasis, *Strongyloides stercoralis*, *Toxocara canis*, *Trichinella*, Whipworm; or protozoa, such as coccidia.

Further examples of parasites include but are not limited to parasites
from the order of Anoplurida, such as *Haematopinus* spp., *Linognathus* spp., *Pediculus* spp., *Phtirus* spp., *Solenopotes* spp., *Linognathus setosus*, *Linognathus vituli*, *Linognathus ovillus*, *Linognathus oviformis*, *Linognathus pedalis*, *Linognathus stenopsis*, *Haematopinus asini macrocephalus*, *Haematopinus eurysternus*, *Haematopinus suis*, *Pediculus humanus capitis*, *Pediculus humanus corporis*, *Phylloera vastatrix*, *Phthirus pubis*, *Solenopotes capillatus;*
from the order of the Mallophagida and the suborders Amblycerina and Ischnocerina, such as *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp., *Bovicola bovis*, *Bovicola ovis*, *Bovicola limbata*, *Damalina bovis*, *Trichodectes canis*, *Felicola subrostratus*, *Bovicola caprae*, *Lepikentron ovis*, *Werneckiella equi*;
from the order of the Diptera and the suborders Nematocerina and Brachycerina, such as *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Ilybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp., *Aedes aegypti*, *Aedes albopictus*, *Aedes taeniorhynchus*, *Anopheles gambiae*, *Anopheles maculipennis*, *Calliphora erythrocephala*, *Chrysozona pluvialis*, *Culex quinquefasciatus*, *Culex pipi-* ens, *Culex tarsalis, Fannia canicularis, Sarcophaga carnaria, Stomoxys calcitrans, Tipula paludosa, Lucilia cuprina, Lucilia sericata, Simulium reptans, Phlebotomus papatasi, Phlebotomus* longipalpis, *Odagmia ornata, Wilhelmia equina, Boophthora erythrocephala, Tabanus bromius, Tabanus spodopterus, Tabanus atratus, Tabanus sudeticus, Hybomitra ciurea, Chrysops caecutiens, Chrysops relictus, Haematopota pluvialis, Haematopota italica, Musca autumnalis, Musca domestica, Haematobia irritans irritans, Haematobia irritans exigua, Haematobia stimulans, Hydrotaea irritans, Hydrotaea albipuncta, Chrysomya chloropyga, Chrysomya bezziana, Oestrus ovis, Hypoderma bovis, Hypoderma lineatum, Przhevalskiana silenus, Dermatobia hominis, Melophagus ovinus, Lipoptena capreoli, Lipoptena cervi, Hippobosca variegata, Hippobosca equina, Gasterophilus intestinalis, Gasterophilus haemorroidalis, Gasterophilus inermis, Gasterophilus nasalis, Gasterophilus nigricornis, Gasterophilus pecorum, Braula cocca;* from the order of the Siphonapterida, such as *Pulex* spp., *Ctenocephalides* spp., *Tunga* spp., *Xenopsylla* spp., *Ceratophyllus* spp., *Ctenocephalides canis, Ctenocephalides felis, Pulex irritans, Tunga penetrans, Xenopsylla cheopis;* from the order of the Heteropterida, such as *Cimex* spp., *Triatoma* spp., *Rhodnius* spp., *Panstrongylus* spp.;

from the order of the Blattarida, such as *Blatta orientalis, Periplaneta americana, Blattela germanica, Supella* spp., *Suppella longipalpa;*

The compounds of the third embodiment are particularly useful for controlling parasites from the subclass of the Acari (Acarina) and the orders of the Meta- and Mesostigmata, such as *Argas* spp., *Ornithodorus* spp., *Otobius* spp., *Ixodes* spp., *Amblyomma* spp., *Rhipicephalus (Boophilus)* spp *Dermacentor* spp., *Haemaphysalis* spp., *Hyalomma* spp., *Dermanyssus* spp., the original genus of multi host ticks, namely *Rhipicephalus* spp., *Ornithonyssus* spp., *Pneumonyssus* spp., *Raillietia* spp., *Pneumonyssus* spp., *Sternostoma* spp., *Varroa* spp., *Acarapis* spp., *Argas persicus, Argas reflexus, Ornithodorus moubata, Otobius megnini, Rhipicephalus (Boophilus) microplus, Rhipicephalus (Boophilus) decoloratus, Rhipicephalus (Boophilus) annulatus, Rhipicephalus (Boophilus) calceratus, Hyalomma anatolicum, Hyalomma aegypticum, Hyalomma marginatum, Hyalomma transiens, Rhipicephalus evertsi, Ixodes ricinus, Ixodes hexagonus, Ixodes canisuga, Ixodes pilosus, Ixodes rubicundus, Ixodes scapularis, Ixodes holocyclus, Haemaphysalis concinna, Haemaphysalis punctata, Haemaphysalis cinnabarina, Haemaphysalis otophila, Haemaphysalis leachi, Haemaphysalis longicorni, Dermacentor marginatus, Dermacentor reticulatus, Dermacentor pictus, Dermacentor albipictus, Dermacentor andcrsoni, Dermacentor variabilis, Hyalomma mauritanicum, Rhipicephalus sanguineus, Rhipicephalus bursa, Rhipicephalus appendiculatus, Rhipicephalus capensis, Rhipicephalus turanicus, Rhipicephalus zambeziensis, Amblyomma americanum, Amblyomma variegatum, Amblyomma maculatum, Amblyomma hebraeum, Amblyomma cajennense, Dermanyssus gallinae, Ornithonyssus bursa, Omithonyssus sylviarum, Varroa jacobsoni;* from the order of the Actinedida (Prostigmata) and Acaridida (Astigmata), such as for example *Acarapis* spp., *Cheyletiella* spp., *Ornithocheylctia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp., *Cheyletiella yasguri, Cheyletiella blakei, Demodex canis, Demodex bovis, Demodex ovis, Demodex caprae, Demodex equi, Demodex caballi, Demodex suis, Neotrombicula autumnalis, Neotrombicula desaleri, Neoschöngastia xerothermobia, Trombicula akamushi, Otodectes cynotis, Notoedres cati, Sarcoptis canis, Sarcoptes bovis, Sarcoptes ovis, Sarcoptes rupicaprae or Sarcoptes caprae, Sarcoptes equi, Sarcoptes suis, Psoroptes ovis, Psoroptes cuniculi, Psoroptes equi, Chorioptes bovis, Psoergates ovis, Pneumonyssoidic Mange, Pneumonyssoides caninum, Acarapis woodi.*

The compounds of the second embodiment are particularly useful for controlling parasites from the subclass of the Acari (Acarina) and the orders of the Meta- and Mesostigmata, with the exception of *Ornithodoros* spp., *Ixodes* spp., and *Boophilus* spp. In particular, the following are mentioned: *Amblyomma* spp., *Dermacentor* spp., *Haemaphysalis* spp., *Hyalomma* spp., *Dermanyssus* spp., *Rhipicephalus* spp., *Ornithonyssus* spp., *Pneumonyssus* spp., *Varroa* spp., *Hyalomma anatolicum, Hyalomma marginatum, Rhipicephalus evertsi, Haemaphysalis leachi, Haemaphysalis longicorni, Dermacentor marginatus, Dermacentor reticulatus, Dermacentor andersoni, Dennacentor variabilis, Hyalomma mauritanicum, Rhipicephalus sanguineus, Rhipicephalus bursa, Rhipicephalus appendiculatus, Rhipicephalus capensis, Rhipicephalus turanicus, Amblyomma americanum, Amblyomma variegatum, Amblyomma maculatum, Amblyomma hebracum, Amblyomma cajennense, Dermanyssus gallinae, Ornithonyssus bursa, Ornithonyssus sylviarum, Varroa jacobsoni;* from the order of the Actinedida (Prostigmata) and Acaridida (Astigmata), such as for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp., *Cheyletiella yasguri, Cheyletiella blakei, Demodex canis, Demodex bovis, Demodex ovis, Demodex caprae, Demodex equi, Demodex caballi, Demodex suis, Neotrombicula autumnalis, Neotrombicula desaleri, Neoschöngastia xerothermobia, Trombicula akamushi, Otodectes cynotis, Notoedres cati, Sarcoptis canis, Sarcoptes bovis, Sarcoptes ovis, Sarcoptes rupicaprae or Sarcoptes caprae, Sarcoptes equi, Sarcoptes suis, Psoroptes ovis, Psoroptes cuniculi, Psoroptes equi, Chorioptes bovis, Psoergates ovis, Pneumonyssoidic Mange, Pneumonyssoides caninum, Acarapis woodi.*

According to a particularly preferred embodiment the compounds of embodiment 1, embodiment 2 or embodiment 3 are used for the control of *Amblyomma americanum*.

According to a further particularly preferred embodiment the compounds of embodiment 1, embodiment 2 or embodiment 3 are used for the control of *Dermacentor variabilis*.

According to a further particularly preferred embodiment the compounds of embodiment 1, embodiment 2 or embodiment 3 are used for the control of *Dermacentor reticulatus*.

According to a further particularly preferred embodiment the compounds of embodiment 1, embodiment 2 or embodiment 3 are used for the control of *Rhipicephalus sanguineus*.

According to a further particularly preferred embodiment the compounds of embodiment 1, embodiment 2 or embodiment 3 are used for the control of *Rhipicephalus decoloratus*.

Diseases transmitted through parasites, particularly ectoparasites are for example bacterial, viral, rickettsial and protozoal vector-borne diseases.

Examples of viral diseases transmitted through arboviruses, i.e. arthropod borne viruses, are Crimean-Congo Hemorhagic Fever (CCHF), Febrile illness, Papataci fever, Encephalitis, Meningitis, which are caused by Bunyaviridae such as Bunyavirus, Nairovirus or Phlebovirus; Bluetongue, meningoencephalits, Febrile illness, hemorhagic fever, which are caused by Reoviridae, such as Orbivirus, Colitivirus; Febrile illness, rash, enzephalitis, polyarthritis, lymphadenitis, which are caused by Togaviridae, such as Sindbisvirus, Chikungunya Virus; tick-borne meningoencephalitis, Dengue hemorhagic fever, encephalitis, Febrile illness, Yellow fever, which are caused by Flaviviridae, such as Flavivirus (including diverse sub-groups).

Examples of bacterial diseases transmitted through parasites are Rickettsiosis, such as Rocky Mountain spotted fever, tick typhus caused by infection through *Rickettsia* ssp; Tularemia caused by infection through *Francisella tularensis*; Borreliosis or Spirochaetosis, such as Lyme disease, or relapsing fever, caused by infection through *Borrelia* ssp.; Ehrllichiosis caused by infection through *Ehrlichia* ssp.; Plague, caused by infection through *Yersinia* ssp.

Examples of protozoal or rickettsial borne diseases are Babesiosis, such as texas fever, red water disease, Q-fever caused by infection through *Babesia* ssp.; Theileriosis, such as east coast fever, Mediterranean coast fever, caused by infection through *Theileria* ssp.; Nagana disease, Sleeping sickness caused by infection through *Trypanosoma* ssp., Anaplasmosis caused by infection through *Anaplasma* ssp.; Malaria caused by infection through *Plasmodium* ssp.; Leishmaniasis caused by infection through *Leishmania* ssp.

The diseases transmitted through parasites are numerous and are not only limited to the above mentioned. Further diseases caused by animal parasites, in particular ectoparasites, are Myiasis caused by parasites like e.g. *Lucilia* ssp.; Scabies caused by parasites like e.g. *Sarcoptes* ssp., *Psoroptes* ssp., *Demodex* ssp.; Pediculosis caused by parasites like Mallophaga (biting lice) *Bovicola* ssp., and Anoplura (sucking lice) *Haematopinus* ssp.; Flea allergic dermatitis caused by parasites like *Ctenocephalides* ssp., *Pulex* ssp.; Hypodermosis caused by parasites like e.g. *Hypoderma* ssp., *Dermatobia* ssp.; Ixodidiosis caused by parasites like e.g. *Ixodes* ssp., *Rhipcephalus* ssp., *Hyalomma* ssp., *Amblyomma* ssp.

According to the invention, the term "animals" include all kind of animals among that also humans, domestic animals, like conventional pet animals, such as for example dogs, cats, cage birds, aquarium fish, less conventional pet animals, such as ferrets, reptiles and exotic birds, all kind of experimental animals, such as rodents like for example, rats and mice, and hamsters and guinea pigs, and agricultural livestock.

Examples for agricultural livestock are cattle, sheep, goats, horses, pigs, donkeys, camels, buffaloes, rabbits, fur animals such as mink; poultry, like chickens, turkeys, ducks, geese; and other agricultural livestock like honeybee.

By controlling animal parasites it is understood to combat the parasites or to prevent infestation through parasites. By combating animal parasites it is understood to reduce the absolute number of parasites on or in the host animal.

The compounds or composition according to the invention can be administered in a known manner and in an appropriate preparation form. Preference is given to enteral, parenteral, or external administration.

Generally, when used for the treatment of animals the active compounds of formula (I) can be applied directly. Preferably they are applied as pharmaceutical compositions which may contain pharmaceutically acceptable excipients and/or auxiliaries which are known in the art.

In the veterinary field and in animal keeping, the active compounds are applied (=administered) in the known manner by enteral administration in the form of, for example, tablets, capsules, drinks, drenches, granules, pastes, boluses, the feed-through method, suppositories; by parenteral administration, such as, for example, by injections (intramuscular, subcutaneous, intravenous, intraperitoneal and the like), implants, by nasal application, by dermal application in the form of, for example, bathing or dipping, spraying, pouring-on and spotting-on, washing, dusting, and with the aid of active-compound-comprising shaped articles such as collars, ear tags, tail tags, limb bands, halters, marking devices and the like. The active compounds may be formulated as shampoo or as suitable formulations usable in aerosols, unpressurized sprays, for example pump sprays and atomizer sprays.

In general, the invention may be carried out in a manner fit to the form of application or administering. Suitable forms include aerosols, unpressurized sprays, for example pump sprays and atomizer sprays, automatic misting devices, foggers, foams, gels, vaporizer products with vaporizer platelets made of cellulose or polymer, liquid vaporizers, gel and membrane vaporizers, propeller-driven vaporizers, vaporization systems which do not consume energy (passive vaporization systems).

Moreover, the compounds and compositions according to the invention can be applied by way of intramuscular, subcutaneous, intravenous, intraperitoneal injections, implants, or nasal application; by dermal application in the form of, for example, bathing or dipping, spraying, pouring-on and spotting-on, washing, dusting, and with the aid of active-compound-comprising shaped articles such as collars, ear tags, tail tags, limb bands, halters, marking devices and the like. The preparation forms for administering the compounds and compositions according to the invention enterally can be tablets, capsules, drinks, drenches, granules, pastes, boluses, feed-through method, and suppositories.

In particular, the compounds and compositions according to the invention can be formulated into usual preparation forms. For the various ways of administration, examples of the preparation forms include solutions, emulsions, wettable powders, dry flowables, suspensions, dusts, foams, pastes, tablets, granules, aerosols, active compound infiltrated-natural and synthetic products, microcapsules, preparations with a combustor (for example, fumigating and smoking cartridges, cans and coils), ULV (cold mists and warm mists). Preference is given to powders, emulsions, flowables, homogeneous solutions, emulsion concentrate formulations, WP and suspensions, or suspension concentrate formulations. Particularly preferred are methods of application, like pour-ons, spot-ons, sprays, ear-tags and dips with the formulations mentioned herein.

Each of these formulations may be prepared by a known manner per se. Usually the compound or composition according to the invention is mixed with developers, such as liquid diluents or carriers, liquid gas diluents or carriers, solid diluents or carriers, and optionally with surfactants, such as anionic, kationic and non-ionic surfactants, such as dioctyl sodium sulfosuccinate and/or dispersants. Additionally to said developers and the optionally present surfactant and/or dispersant other auxiliary ingredients, like emulsifiers, foam former or anti-foaming agents, such as simethicone, preservatives, binders and/or colorants can be present in the formulation. The formulation of the active compound or composition preferably comprises a developer, an emulsifiers and/or dispersants and/or foam formers.

Examples of liquid diluents or carriers include, but are not limited to, aromatic hydrocarbons, such as xylene, toluene and alkylnaphthalene, chlorinated aromatic or aliphatic hydrocarbons, such as chlorobenzenes, ethylene chlorides and methylene chlorides, aliphatic hydrocarbons, such as cyclohexane, paraffins, such as mineral oil fractions, alcohols, such as for example, benzyl alcohol, isopropanol, ethanol, butanol, glycol and ethers and esters thereof, ketones, such as acetone, methyl ethyl ketone, methyl isobutyl ketone and cyclohexanone, strong polar solvents, such as dimethylformamide and dimethylsulfoxide, cyclic carbonates, such as ethylene carbonate, propylene carbonate, pyrrolidones, such as N-octylpyrrolidone, N-methylpyrrolidone, ethers, such as diethylene glycol monomethylether and diethylene glycol monopropylether, lactones, such as butyrolacton, and water.

Examples of liquid gas diluents or carriers include, but are not limited to, those which are in a gaseous state at room pressure and liquid under increased pressure, like for example aerosols propellants, such as fron, propane, nitrogen gas, carbon dioxide, and halogenated hydrocarbons.

Examples of solid diluents or carrier include, but are not limited to, ground natural minerals, such as kaolins, clays, talc, chalk, quartz, attapulgite, montmorillonite or diatomaceous earth, and ground synthetic minerals, such as highly dispersed silicic acid, alumina and silicate.

Examples of solid carriers for granules include, but are not limited to, crushed and fractionated rocks, like for example, calcite, marble, pumice, sepiolite and dolomite, synthetic granules of inorganic or organic powders, organic materials, like for example, sawdust, coconut shells, maize cobs and tobacco stalks.

Examples of emulsifiers and/or foam formers include, but are not limited to, nonionic and anionic emulsifiers, like for example, polyoxyethylene fatty acid esters, polyoxyethylene fatty acid alcohol ethers, such as for example, alkylaryl polyglycol ether, alkyl sulfonates, alkyl sulfates and aryl sulfonates and albumin hydrolysates.

Examples of active-compounds comprising shaped articles, such as for example collars include but are not limited o poly vinyl chloride, polyamide, polyamide$_6$, polyamide-$_{6,6}$, polyolefines such as high densitiy polyethylene (HDPE), polyethylene, polypropylene and ethylene propylene diene monomer (EPDM).

Examples of dispersants include, but are not limited to, lignin sulfite waste liquor and methylcellulose.

Binders are used in preparations, like for example, powders, granules and emulsifiable concentrates. Examples of binders include, but are not limited to, starches, sugars, cellulose, or modified cellulose such as carboxymethylcellulose, hydroxypropyl cellulose, lactose, or sugar alcohols like xylitol, sorbitol or maltitol, natural or synthetic polymers, such as, gum arabicum, xanthane, polyvinyl alcohol and polyvinyl acetate.

Examples of the colorant include, but are not limited to, inorganic pigments, such as iron oxide, titanium oxide and Prussian blue, organic colorants such as Alizarin colorants, azo colorants or metal phthalocyanine colorants, and further, trace nutrients such as salts of iron, manganese, boron, copper, cobalt, molybdenum or zinc.

The formulation may contain the compound according to the invention from 0.1 to 95% by weight of the total preparation, preferably from 0.5 to 90% by weight, most preferred from 0.8 to 70% by weight.

TABLE 1

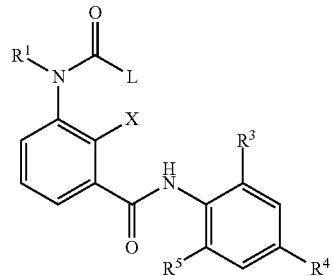

I-1

| No. | L | $R^1$ | $R^3$ | $R^4$ | $R^5$ | X | M.p (° C.) |
|---|---|---|---|---|---|---|---|
| I-1-1 | 4-(trifluoromethyl)pyridin-3-yl | H | $CH_3$ | $CF(CF_3)_2$ | $C_2H_5$ | H | 176-179 |
| I-1-2 | 4,6-difluoropyridin-3-yl | H | $CH_3$ | $CF(CF_3)_2$ | $C_2H_5$ | H | 181-182 |
| I-1-3 | 6-chloropyridin-3-yl | H | $CH_3$ | $CF(CF_3)_2$ | $C_2H_5$ | H | 237-238 |
| I-1-4 | 6-chloropyridin-3-yl | H | $CH_3$ | $CF(CF_3)_2$ | $CH_3$ | H | |
| I-1-5 | 2-fluoropyridin-3-yl | H | $CH_3$ | $CF(CF_3)_2$ | $C_2H_5$ | H | 102-105 |
| I-1-6 | 2-chloropyridin-3-yl | H | $CH_3$ | $CF(CF_3)_2$ | $C_2H_5$ | H | 121-124 |
| I-1-7 | 2-bromopyridin-3-yl | H | $CH_3$ | $CF(CF_3)_2$ | $C_2H_5$ | H | 118-120 |
| I-1-8 | 5-chloropyridin-3-yl | H | $CH_3$ | $CF(CF_3)_2$ | $C_2H_5$ | H | |
| I-1-9 | 2-methylpyridin-3-yl | H | $CH_3$ | $CF(CF_3)_2$ | $CH_3$ | H | |
| I-1-10 | 2-methylpyridin-3-yl | H | $CH_3$ | $CF(CF_3)_2$ | $C_2H_5$ | H | |
| I-1-11 | pyridin-3-yl | H | $CH_3$ | $CF(CF_3)_2$ | $CH_3$ | H | |
| I-1-12 | pyridin-3-yl | H | $CH_3$ | $CF(CF_3)_2$ | $C_2H_5$ | H | |
| I-1-13 | 3-chloro-5-(trifluoromethyl)pyridin-2-yl | H | $CH_3$ | $CF(CF_3)_2$ | $C_2H_5$ | H | 203-205 |
| I-1-14 | 3,5-dichloropyridin-2-yl | H | $CH_3$ | $CF(CF_3)_2$ | $C_2H_5$ | H | |
| I-1-15 | 3-chloropyridin-2-yl | H | $CH_3$ | $CF(CF_3)_2$ | $C_2H_5$ | H | >250 |
| I-1-16 | 3-(trifluoromethyl)pyridin-2-yl | H | $CH_3$ | $CF(CF_3)_2$ | $CH_3$ | H | |

TABLE 1-continued

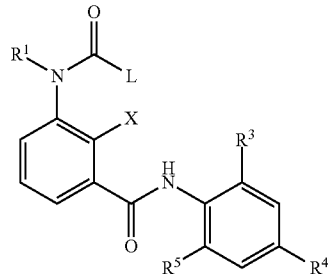

I-1

| No. | L | R¹ | R³ | R⁴ | R⁵ | X | M.p (° C.) |
|---|---|---|---|---|---|---|---|
| I-1-17 | 3-(trifluoromethyl)pyridin-2-yl | H | CH₃ | CF(CF₃)₂ | C₂H₅ | H | |
| I-1-18 | pyridin-2-yl | H | CH₃ | CF(CF₃)₂ | CH₃ | H | |
| I-1-19 | pyridin-2-yl | H | CH₃ | CF(CF₃)₂ | C₂H₅ | H | |
| I-1-20 | 2,6-dichloropyridin-4-yl | H | CH₃ | CF(CF₃)₂ | C₂H₅ | H | 140-144 |
| I-1-21 | 2-chloropyridin-4-yl | H | CH₃ | CF(CF₃)₂ | C₂H₅ | H | 115-118 |
| I-1-22 | pyridin-4-yl | H | CH₃ | CF(CF₃)₂ | CH₃ | H | |
| I-1-23 | pyridin-4-yl | H | CH₃ | CF(CF₃)₂ | C₂H₅ | H | |
| I-1-24 | 2,5-dichlorothiophen-3-yl | H | CH₃ | CF(CF₃)₂ | C₂H₅ | H | 90-94 |
| I-1-25 | 2-chlorothiophen-3-yl | H | CH₃ | CF(CF₃)₂ | C₂H₅ | H | |
| I-1-26 | thiophen-3-yl | H | CH₃ | CF(CF₃)₂ | C₂H₅ | H | |
| I-1-27 | 5-chlorothiophen-2-yl | H | CH₃ | CF(CF₃)₂ | C₂H₅ | H | |
| I-1-28 | 3-chlorothiophen-2-yl | H | CH₃ | CF(CF₃)₂ | CH₃ | H | |
| I-1-29 | 3-chlorothiophen-2-yl | H | CH₃ | CF(CF₃)₂ | C₂H₅ | H | 90-95 |
| I-1-30 | thiophen-2-yl | H | CH₃ | CF(CF₃)₂ | C₂H₅ | H | 182 |
| I-1-31 | thiophen-2-yl | H | CH₃ | CF(CF₃)₂ | CH₃ | H | |
| I-1-32 | furan-2-yl | H | CH₃ | CF(CF₃)₂ | C₂H₅ | H | 97-99 |
| I-1-33 | furan-2-yl | H | CH₃ | CF(CF₃)₂ | CH₃ | H | |
| I-1-34 | 3-(tert-butyl)-1-methylpyrazol-5-yl | H | CH₃ | CF(CF₃)₂ | C₂H₅ | H | 102-106 |
| I-1-35 | 4-methyl-1,2,3-thiadiazol-5-yl | H | CH₃ | CF(CF₃)₂ | C₂H₅ | H | 223-224 |
| I-1-36 | 2-iodophenyl | H | CH₃ | CF(CF₃)₂ | C₂H₅ | H | 134-141 |
| I-1-37 | 2-chlorophenyl | H | CH₃ | CF(CF₃)₂ | I | H | 101-105 |
| I-1-38 | 2-chlorophenyl | H | CH₃ | CF(CF₃)₂ | C₂F₅ | H | 91-96 |
| I-1-39 | 4-(trifluoromethoxy)phenyl | H | CH₃ | CF(CF₃)₂ | C₂H₅ | H | 153-155 |
| I-1-40 | 2-bromophenyl | H | CH₃ | CF(CF₃)₂ | C₂H₅ | H | 105-109 |
| I-1-41 | 3-bromophenyl | H | CH₃ | CF(CF₃)₂ | C₂H₅ | H | 164-167 |
| I-1-42 | 4-bromophenyl | H | CH₃ | CF(CF₃)₂ | C₂H₅ | H | 205-206 |
| I-1-43 | 3,4-dichlorophenyl | H | CH₃ | CF(CF₃)₂ | C₂H₅ | H | 133-135 |
| I-1-44 | 2,4-dichlorophenyl | H | CH₃ | CF(CF₃)₂ | C₂H₅ | H | 129-134 |
| I-1-45 | 3,5-dichlorophenyl | H | CH₃ | CF(CF₃)₂ | C₂H₅ | H | 175-176 |
| I-1-46 | 2,6-dichlorophenyl | H | CH₃ | CF(CF₃)₂ | C₂H₅ | H | 137-140 |
| I-1-47 | 2,3-dichlorophenyl | H | CH₃ | CF(CF₃)₂ | C₂H₅ | H | 123-128 |
| I-1-48 | 2,5-dichlorophenyl | H | CH₃ | CF(CF₃)₂ | C₂H₅ | H | 115-120 |
| I-1-49 | 4-(trifluoromethyl)phenyl | H | CH₃ | CF(CF₃)₂ | C₂H₅ | H | 195-197 |
| I-1-50 | 3-(trifluoromethyl)phenyl | H | CH₃ | CF(CF₃)₂ | C₂H₅ | H | |
| I-1-51 | 2-(trifluoromethyl)phenyl | H | CH₃ | CF(CF₃)₂ | C₂H₅ | H | 134-139 |
| I-1-52 | 2,4,6-trifluorophenyl | H | CH₃ | CF(CF₃)₂ | C₂H₅ | H | 223-224 |
| I-1-53 | 2-nitrophenyl | H | CH₃ | CF(CF₃)₂ | C₂H₅ | H | 110-115 |
| I-1-54 | 2,6-difluorophenyl | H | CH₃ | CF(CF₃)₂ | C₂H₅ | H | 118-121 |
| I-1-55 | 2,3-difluorophenyl | H | CH₃ | CF(CF₃)₂ | C₂H₅ | H | 165-167 |
| I-1-56 | 2,4-difluorophenyl | H | CH₃ | CF(CF₃)₂ | C₂H₅ | H | 187-188 |
| I-1-57 | 2-chlorophenyl | H | CH₃ | CF(CF₃)₂ | C₂H₅ | H | 114-120 |
| I-1-58 | 3-chlorophenyl | H | CH₃ | CF(CF₃)₂ | C₂H₅ | H | 162-165 |
| I-1-59 | 4-chlorophenyl | H | CH₃ | CF(CF₃)₂ | C₂H₅ | H | 163-168 |
| I-1-60 | 4-methoxyphenyl | H | CH₃ | CF(CF₃)₂ | C₂H₅ | H | 192-194 |
| I-1-61 | 4-fluorophenyl | H | CH₃ | CF(CF₃)₂ | C₂H₅ | H | 174-176 |
| I-1-62 | 3-fluorophenyl | H | CH₃ | CF(CF₃)₂ | C₂H₅ | H | 175-177 |
| I-1-63 | 2-fluorophenyl | H | CH₃ | CF(CF₃)₂ | C₂H₅ | H | 164-166 |
| I-1-64 | 4-methylphenyl | H | CH₃ | CF(CF₃)₂ | C₂H₅ | H | 213-214 |
| I-1-65 | 3-methylphenyl | H | CH₃ | CF(CF₃)₂ | C₂H₅ | H | |
| I-1-66 | 2-methylphenyl | H | CH₃ | CF(CF₃)₂ | C₂H₅ | H | 106-112 |
| I-1-67 | phenyl | H | CH₃ | CF(CF₃)₂ | C₂H₅ | H | |
| I-1-68 | 4-(trifluoromethoxy)phenyl | H | CH₃ | CF(CF₃)₂ | CH₃ | H | |
| I-1-69 | 2,3-dichlorophenyl | H | CH₃ | CF(CF₃)₂ | CH₃ | H | |
| I-1-70 | 2,5-dichlorophenyl | H | CH₃ | CF(CF₃)₂ | CH₃ | H | |
| I-1-71 | 4-(trifluoromethyl)phenyl | H | CH₃ | CF(CF₃)₂ | CH₃ | H | |
| I-1-72 | 2,6-difluorophenyl | H | CH₃ | CF(CF₃)₂ | CH₃ | H | 145-148 |

TABLE 1-continued

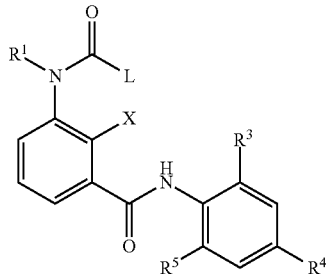

I-1

| No. | L | R¹ | R³ | R⁴ | R⁵ | X | M.p (° C.) |
|---|---|---|---|---|---|---|---|
| I-1-73 | 2,3-difluorophenyl | H | $CH_3$ | $CF(CF_3)_2$ | $CH_3$ | H | |
| I-1-74 | 2,4-difluorophenyl | H | $CH_3$ | $CF(CF_3)_2$ | $CH_3$ | H | |
| I-1-75 | 2-chlorophenyl | H | $CH_3$ | $CF(CF_3)_2$ | $CH_3$ | H | 141-145 |
| I-1-76 | 3-chlorophenyl | H | $CH_3$ | $CF(CF_3)_2$ | $CH_3$ | H | |
| I-1-77 | 4-chlorophenyl | H | $CH_3$ | $CF(CF_3)_2$ | $CH_3$ | H | NMR |
| I-1-78 | 4-ethoxyphenyl | H | $CH_3$ | $CF(CF_3)_2$ | $CH_3$ | H | |
| I-1-79 | 4-(trifluoromethylthio)phenyl | H | $CH_3$ | $CF(CF_3)_2$ | $CH_3$ | H | |
| I-1-80 | 3-fluorophenyl | H | $CH_3$ | $CF(CF_3)_2$ | $CH_3$ | H | |
| I-1-81 | 2-fluorophenyl | H | $CH_3$ | $CF(CF_3)_2$ | $CH_3$ | H | |
| I-1-82 | 4-methylsulfinylphenyl | H | $CH_3$ | $CF(CF_3)_2$ | $CH_3$ | H | |
| I-1-83 | 4-(trifluoromethylsulfinyl)phenyl | H | $CH_3$ | $CF(CF_3)_2$ | $CH_3$ | H | |
| I-1-84 | 4-methylsulfonylphenyl | H | $CH_3$ | $CF(CF_3)_2$ | $CH_3$ | H | |
| I-1-85 | 4-(trifluoromethylsulfonyl)phenyl | H | $CH_3$ | $CF(CF_3)_2$ | $CH_3$ | H | |
| I-1-86 | 2-methylphenyl | H | $CH_3$ | $CF(CF_3)_2$ | $CH_3$ | H | |
| I-1-87 | phenyl | H | $CH_3$ | $C_2F_5$ | $CH_3$ | H | |
| I-1-88 | phenyl | H | $CH_3$ | $CF(CF_3)_2$ | $CH_3$ | H | 201-204 |
| I-1-89 | 4-chlorophenyl | H | $CH_3$ | $CF(CF_3)_2$ | $CH(CH_3)_2$ | H | |
| I-1-90 | 2-fluorophenyl | H | $CH_3$ | $CF(CF_3)_2$ | $CH(CH_3)_2$ | H | |
| I-1-91 | 4-chlorophenyl | H | $C_2H_5$ | $CF(CF_3)_2$ | $C_2H_5$ | H | |
| I-1-92 | 2,6-difluorophenyl | H | $C_2H_5$ | $CF(CF_3)_2$ | $C_2H_5$ | H | |
| I-1-93 | 4-fluorophenyl | H | Cl | $SCF_3$ | Cl | H | |
| I-1-94 | 3-fluorophenyl | H | Cl | $SC_2F_5$ | Cl | H | |
| I-1-95 | 2-fluorophenyl | H | Cl | $SC_3F_7$-n | Cl | H | |
| I-1-96 | 2-chlorophenyl | H | Cl | $S(O)CF_3$ | Cl | H | |
| I-1-97 | 3-chlorophenyl | H | Cl | $S(O)C_2F_5$ | Cl | H | |
| I-1-98 | 4-chlorophenyl | H | Cl | $S(O)C_3F_7$-n | Cl | H | |
| I-1-99 | 2,6-difluorophenyl | H | Cl | $SO_2CF_3$ | Cl | H | |
| I-1-100 | 2,3-difluorophenyl | H | Cl | $SO_2S_2F_5$ | Cl | H | |
| I-1-101 | 2,4-difluorophenyl | H | Cl | $SO_2C_3F_7$-n | Cl | H | |
| I-1-102 | 4-chlorophenyl | H | $CH_3$ | $SCF_3$ | $CH_3$ | H | |
| I-1-103 | 4-fluorophenyl | H | $CH_3$ | $SC_2F_5$ | $CH_3$ | H | |
| I-1-104 | 2-fluorophenyl | H | $CH_3$ | $SC_3F_7$-n | $CH_3$ | H | |
| I-1-105 | 2,4-difluorophenyl | H | $CH_3$ | $SO_2C_3F_7$-n | $CH_3$ | H | |
| I-1-106 | 4-methylthiophenyl | H | $CH_3$ | $CF(CF_3)_2$ | $CH_3$ | H | |
| I-1-107 | 4-(trifluoromethyl)pyridin-3-yl | H | $CH_3$ | $CF(CF_3)_2$ | $C_2H_5$ | F | |
| I-1-108 | 4,6-difluoropyridin-3-yl | H | $CH_3$ | $CF(CF_3)_2$ | $CH_3$ | F | |
| I-1-109 | 6-chloropyridin-3-yl | H | $CH_3$ | $CF(CF_3)_2$ | $CH_3$ | F | |
| I-1-110 | 3-chloro-5-(trifluoromethyl)pyridin-2-yl | H | $CH_3$ | $CF(CF_3)_2$ | $C_2H_5$ | F | |
| I-1-111 | 2-bromophenyl | H | $CH_3$ | $CF(CF_3)_2$ | $C_2H_5$ | F | |
| I-1-112 | 3,4-dichlorophenyl | H | $CH_3$ | $CF(CF_3)_2$ | $C_2H_5$ | F | |
| I-1-113 | 2,4-dichlorophenyl | H | $CH_3$ | $CF(CF_3)_2$ | $C_2H_5$ | F | |
| I-1-114 | 2,6-dichlorophenyl | H | $CH_3$ | $CF(CF_3)_2$ | $C_2H_5$ | F | |
| I-1-115 | 2,3-dichlorophenyl | H | $CH_3$ | $CF(CF_3)_2$ | $C_2H_5$ | F | |
| I-1-116 | 2,5-dichlorophenyl | H | $CH_3$ | $CF(CF_3)_2$ | $C_2H_5$ | F | |
| I-1-117 | 3-(trifluoromethyl)phenyl | H | $CH_3$ | $CF(CF_3)_2$ | $C_2H_5$ | F | |
| I-1-118 | 2-(trifluoromethyl)phenyl | H | $CH_3$ | $CF(CF_3)_2$ | $C_2H_5$ | F | |
| I-1-119 | 2,4,6-trifluorophenyl | H | $CH_3$ | $CF(CF_3)_2$ | $C_2H_5$ | F | |
| I-1-120 | 2-nitrophenyl | H | $CH_3$ | $CF(CF_3)_2$ | $C_2H_5$ | F | |
| I-1-121 | 2,6-difluorophenyl | H | $CH_3$ | $CF(CF_3)_2$ | $C_2H_5$ | F | |
| I-1-122 | 2,3-difluorophenyl | H | $CH_3$ | $CF(CF_3)_2$ | $C_2H_5$ | F | |
| I-1-123 | 2,4-difluorophenyl | H | $CH_3$ | $CF(CF_3)_2$ | $C_2H_5$ | F | |
| I-1-124 | 2-chlorophenyl | H | $CH_3$ | $CF(CF_3)_2$ | $C_2H_5$ | F | |
| I-1-125 | 3-chlorophenyl | H | $CH_3$ | $CF(CF_3)_2$ | $C_2H_5$ | F | |
| I-1-126 | 4-chlorophenyl | H | $CH_3$ | $CF(CF_3)_2$ | $C_2H_5$ | F | |
| I-1-127 | 3-fluorophenyl | H | $CH_3$ | $CF(CF_3)_2$ | $C_2H_5$ | F | |
| I-1-128 | 2-fluorophenyl | H | $CH_3$ | $CF(CF_3)_2$ | $C_2H_5$ | F | |

TABLE 1-continued

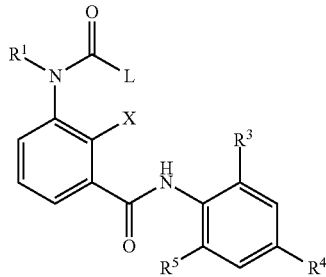

I-1

| No. | L | $R^1$ | $R^3$ | $R^4$ | $R^5$ | X | M.p (° C.) |
|---|---|---|---|---|---|---|---|
| I-1-129 | 2,3-dichlorophenyl | H | $CH_3$ | $CF(CF_3)_2$ | $CH_3$ | F | |
| I-1-130 | 2,5-dichlorophenyl | H | $CH_3$ | $CF(CF_3)_2$ | $CH_3$ | F | |
| I-1-131 | 2,6-difluorophenyl | H | $CH_3$ | $CF(CF_3)_2$ | $CH_3$ | F | |
| I-1-132 | 2,3-difluorophenyl | H | $CH_3$ | $CF(CF_3)_2$ | $CH_3$ | F | |
| I-1-133 | 2,4-difluorophenyl | H | $CH_3$ | $CF(CF_3)_2$ | $CH_3$ | F | |
| I-1-134 | 2-chlorophenyl | H | $CH_3$ | $CF(CF_3)_2$ | $CH_3$ | F | 193-194 |
| I-1-135 | 3-chlorophenyl | H | $CH_3$ | $CF(CF_3)_2$ | $CH_3$ | F | |
| I-1-136 | 3-fluorophenyl | H | $CH_3$ | $CF(CF_3)_2$ | $CH_3$ | F | |
| I-1-137 | 2-fluorophenyl | H | $CH_3$ | $CF(CF_3)_2$ | $CH_3$ | F | |
| I-1-138 | 2-methylphenyl | H | $CH_3$ | $CF(CF_3)_2$ | $CH_3$ | F | |
| I-1-139 | 4-chlorophenyl | H | $CH_3$ | $CF(CF_3)_2$ | $CH_3$ | F | 183-184 |
| I-1-140 | 3,5-dichlorophenyl | H | $CH_3$ | $CF(CF_3)_2$ | $C_2H_5$ | Cl | |
| I-1-141 | 4-bromophenyl | H | $CH_3$ | $CF(CF_3)_2$ | $C_2H_5$ | Cl | |
| I-1-142 | 2-chlorophenyl | H | $CH_3$ | $CF(CF_3)_2$ | $CH_3$ | Cl | >250 |
| I-1-143 | 2-chlorophenyl | H | $CH_3$ | $CF(CF_3)_2$ | $CH_3$ | $CH_3$ | >250 |
| I-1-144 | 3-methoxy-5-(trifluoromethyl)thiophen-2-yl | H | $CH_3$ | $CF(CF_3)_2$ | $C_2H_5$ | H | 230-231 |
| I-1-145 | 5-chloro-1-methyl-3-(trifluoromethyl)pyrazole | H | $CH_3$ | $CF(CF_3)_2$ | $C_2H_5$ | H | 101-106 |
| I-1-146 | 4-bromo-1-ethyl-3-methylpyrazol-5-yl | H | $CH_3$ | $CF(CF_3)_2$ | $C_2H_5$ | H | 91-97 |
| I-1-147 | 5-methylisoxazol-4-yl | H | $CH_3$ | $CF(CF_3)_2$ | $C_2H_5$ | H | 216-217 |
| I-1-148 | isoxazol-5-yl | H | $CH_3$ | $CF(CF_3)_2$ | $C_2H_5$ | H | 91-99 |
| I-1-149 | 2-chloropyridin-3-yl | H | $CH_3$ | $CF(CF_3)_2$ | $CH_3$ | H | 120-124 |
| I-1-150 | 6-fluoropyridin-3-yl | H | $CH_3$ | $CF(CF_3)_2$ | $C_2H_5$ | H | 211-213 |
| I-1-151 | 6-fluoropyridin-3-yl | H | $CH_3$ | $CF(CF_3)_2$ | $CH_3$ | H | >250 |
| I-1-152 | 3-hydroxypyridin-2-yl | H | $CH_3$ | $CF(CF_3)_2$ | $C_2H_5$ | H | 228-230 |
| I-1-153 | 4-(trifluoromethyl)pyridin-2-yl | H | $CH_3$ | $CF(CF_3)_2$ | $CH_3$ | H | >250 |
| I-1-154 | 6-chloro-4-(trifluoromethyl)pyridin-3-yl | H | $CH_3$ | $CF(CF_3)_2$ | $C_2H_5$ | H | 223-227 |
| I-1-155 | (E)-propenyl | H | $CH_3$ | $CF(CF_3)_2$ | $CH_3$ | H | NMR |
| I-1-156 | 2-chlorocyclohex-1-ene-1-yl | H | $CH_3$ | $CF(CF_3)_2$ | $CH_3$ | H | NMR |
| I-1-157 | methylidenecyclohexane-2-yl | H | CH | $CF(CF_3)_2$ | $C_2H_5$ | H | NMR |
| I-1-158 | (Z)-2-fluorostyrene-2-yl | H | $CH_3$ | $CF(CF_3)_2$ | $C_2H_5$ | H | NMR |
| I-1-159 | (E)-but-2-en-2-yl | H | $CH_3$ | $CF(CF_3)_2$ | $C_2H_5$ | H | NMR |
| I-1-160 | (Z)-but-2-en-2-yl | H | $CH_3$ | $CF(CF_3)_2$ | $C_2H_5$ | H | NMR |
| I-1-161 | (E)-1-chloroethene-1-yl | H | $CH_3$ | $CF(CF_3)_2$ | $C_2H_5$ | H | NMR |
| I-1-162 | cyclopropyl | H | $CH_3$ | $CF(CF_3)_2$ | $C_2H_5$ | H | NMR |
| I-1-163 | (E)-2-methylstyrene-2-yl | H | $CH_3$ | $CF(CF_3)_2$ | $C_2H_5$ | H | NMR |
| I-1-164 | (E)-but-2-en-2-yl | H | $CH_3$ | $CF(CF_3)_2$ | $CH_3$ | H | NMR |
| I-1-165 | (E)-but-2-en-2-yl | H | $CH_3$ | $CF(CF_3)_2$ | $C_2H_5$ | H | NMR |
| I-1-166 | (E)-pent-2-en-2-yl | H | $CH_3$ | $CF(CF_3)_2$ | $C_2H_5$ | H | NMR |
| I-1-167 | cyclohexen-1-yl | H | $CH_3$ | $CF(CF_3)_2$ | $C_2H_5$ | H | NMR |
| I-1-168 | cyclopenten-1-yl | H | $CH_3$ | $CF(CF_3)_2$ | $C_2H_5$ | H | NMR |
| I-1-169 | (E)-pent-2-en-2-yl | H | $CH_3$ | $CF(CF_3)_2$ | $CH_3$ | H | NMR |
| I-1-170 | cyclohexen-1-yl | H | $CH_3$ | $CF(CF_3)_2$ | $CH_3$ | H | NMR |
| I-1-171 | (E)-but-2-en-2-yl | H | I | $CF(CF_3)_2$ | I | H | NMR |
| I-1-172 | (E)-but-2-en-2-yl | H | I | $CF_3$ | I | H | NMR |
| I-1-173 | 2-fluorophenyl | H | I | $CF(CF_3)_2$ | I | H | NMR |
| I-1-174 | 2-fluorophenyl | H | Br | $CF(CF_3)_2$ | Br | H | NMR |
| I-1-175 | phenyl | H | I | $CF(CF_3)_2$ | I | H | NMR |
| I-1-176 | 2-chloro-pyridin-5-yl | H | I | $CF(CF_3)_2$ | I | H | NMR |
| I-1-177 | cyclopenten-1-yl | H | I | $CF(CF_3)_2$ | I | H | NMR |
| I-1-178 | 2-fluorophenyl | H | I | $CF(CF_3)_2$ | Br | H | NMR |
| I-1-179 | 1-methoxyiminoethanal-1-yl | H | $CH_3$ | $CF(CF_3)_2$ | $C_2H_5$ | H | 74-77 |
| I-1-180 | 2-chlorophenyl | H | $CH_3$ | $SC_3F_7$ | $CH_3$ | H | 108-112 |

TABLE 1-continued

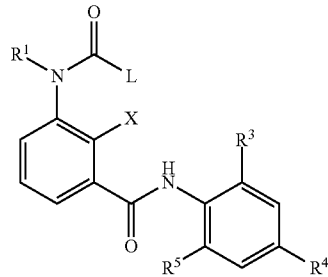

I-1

| No. | L | R¹ | R³ | R⁴ | R⁵ | X | M.p (° C.) |
|---|---|---|---|---|---|---|---|
| I-1-181 | 2-fluorophenyl | H | $CH_3$ | $SC_3F_7$ | $CH_3$ | H | 162-163 |
| I-1-182 | 2,6-difluorophenyl | H | $CH_3$ | $SC_3F_7$ | $CH_3$ | H | 105-110 |
| I-1-183 | 2,5-difluorophenyl | H | $CH_3$ | $CF(CF_3)_2$ | $C_2H_5$ | H | 170-175 |
| I-1-184 | 2-fluorophenyl | H | $C_2H_5$ | $CF(CF_3)_2$ | $C_2H_5$ | H | 185-186 |
| I-1-185 | 2,6-difluorophenyl | H | $C_2H_5$ | $CF(CF_3)_2$ | $C_2H_5$ | H | 202-203 |
| I-1-186 | 2-fluorophenyl | H | $CH_3$ | $SCF_3$ | $C_2H_5$ | H | 75-78 |
| I-1-187 | 2-fluorophenyl | H | $CH_3$ | $SC_2F_5$ | $C_2H_5$ | H | 83-89 |
| I-1-188 | 2-chloro-6-fluorophenyl | H | $CH_3$ | $CF(CF_3)_2$ | $C_2H_5$ | H | NMR |
| I-1-189 | 2-fluorophenyl | H | $CH_3$ | $CF(CF_3)_2$ | $C_2H_5$ | H | NMR |
| I-1-190 | 2-ethylphenyl | H | $CH_3$ | $CF(CF_3)_2$ | $C_2H_5$ | H | 119-122 |
| I-1-191 | phenyl | H | $CH_3$ | $CF(CF_3)_2$ | $C_2H_5$ | F | 194-195 |
| I-1-192 | 2-chlorophenyl | H | $CH_3$ | $CF(CF_3)_2$ | $C_2H_5$ | F | 201-202 |
| I-1-193 | 3-chlorophenyl | H | $CH_3$ | $CF(CF_3)_2$ | $C_2H_5$ | F | 86-89 |
| I-1-194 | 4-chlorophenyl | H | $CH_3$ | $CF(CF_3)_2$ | $C_2H_5$ | F | 100-103 |
| I-1-195 | 2-fluorophenyl | H | $CH_3$ | $CF(CF_3)_2$ | $C_2H_5$ | F | 161-163 |
| I-1-196 | 3-fluorophenyl | H | $CH_3$ | $CF(CF_3)_2$ | $C_2H_5$ | F | 125-129 |
| I-1-197 | 4-fluorophenyl | H | $CH_3$ | $CF(CF_3)_2$ | $C_2H_5$ | F | 169-173 |
| I-1-198 | 3-fluorophenyl | H | $C_2H_5$ | $CF(CF_3)_2$ | $C_2H_5$ | H | 184-186 |
| I-1-199 | 4-fluorophenyl | H | $C_2H_5$ | $CF(CF_3)_2$ | $C_2H_5$ | H | 180-183 |
| I-1-200 | 4-fluorophenyl | H | $CH_3$ | $SC_3F_7$ | $C_2H_5$ | H | 181-182 |
| I-1-201 | 2-fluorophenyl | H | $CH_3$ | $S(=O)CH_2CF_3$ | $C_2H_5$ | H | 121-125 |
| I-1-202 | 2-fluorophenyl | H | $CH_3$ | $S(=O)_2CH_2CF_3$ | $C_2H_5$ | H | 108-114 |
| I-1-203 | 2-fluorophenyl | H | I | $CF_3$ | $CF_3$ | H | 234-236 |
| I-1-204 | phenyl | H | I | $CF_3$ | $CF_3$ | H | 234-235 |
| I-1-205 | phenyl | H | Br | Br | Br | H | 248-250 |
| I-1-206 | 4-chlorophenyl | H | I | $CF_3$ | $CF_3$ | H | NMR |
| I-1-207 | 2-fluorophenyl | H | I | $CF_3$ | I | H | 243-245 |
| I-1-208 | 2-fluoropyridin-3-yl | H | I | $CF_3$ | I | H | NMR |
| I-1-209 | pyridin-3-yl | H | I | $CF(CF_3)_2$ | I | H | NMR |
| I-1-210 | pyridin-2-yl | H | I | $CF(CF_3)_2$ | I | H | 213-217 |
| I-1-211 | 4-chlorophenyl | H | I | $CF_3$ | $CF_3$ | H | NMR |
| I-1-212 | 4-chlorophenyl | H | Br | Br | $CF_3$ | H | 242-244 |
| I-1-213 | 2-fluorophenyl | H | Br | $SF_5$ | Br | H | 231-232 |
| I-1-214 | 2-bromo-furan-5-yl | H | $CH_3$ | $CF(CF_3)_2$ | $C_2H_5$ | H | 102-107 |
| I-1-215 | 2-chloro-thiophene-5-yl | H | $CH_3$ | $CF(CF_3)_2$ | $C_2H_5$ | H | 183-185 |
| I-1-216 | 3-chloro-thiophene-2-yl | H | $C_2H_5$ | $CF(CF_3)_2$ | $C_2H_5$ | H | 92-98 |
| I-1-217 | 2-chloro-thiophene-5-yl | H | $CH_3$ | $CF(CF_3)_2$ | $C_2H_5$ | H | 195-198 |
| I-1-218 | 3-methyl-thiophene-2-yl | H | $CH_3$ | $CF(CF_3)_2$ | $C_2H_5$ | H | 89-97 |
| I-1-219 | thiophene-2-yl | H | $C_2H_5$ | $CF(CF_3)_2$ | $C_2H_5$ | H | 245-247 |
| I-1-220 | thiophene-2-yl | H | $CH_3$ | $SC_3F_7$ | $C_2H_5$ | H | 92-97 |
| I-1-221 | thiophene-2-yl | H | $CH_3$ | $CF(CF_3)_2$ | $CH_3$ | H | 184-188 |
| I-1-222 | thiophene-3-yl | H | $CH_3$ | $CF(CF_3)_2$ | $C_2H_5$ | H | 167-170 |
| I-1-223 | furan-3-yl | H | $CH_3$ | $CF(CF_3)_2$ | $C_2H_5$ | H | 153-156 |
| I-1-224 | furan-2-yl | H | $CH_3$ | $CF(CF_3)_2$ | $CH_3$ | H | 80-84 |
| I-1-225 | 2,3-dibromo-furan-5-yl | H | $CH_3$ | $CF(CF_3)_2$ | $C_2H_5$ | H | 172-176 |
| I-1-226 | formyl | H | $CH_3$ | $CF(CF_3)_2$ | $CH_3$ | H | 86-90 |
| I-1-227 | 4-methyl-1,2,3-thiadiazole-5-yl | H | $CH_3$ | $CF(CF_3)_2$ | $CH_3$ | H | 230-232 |
| I-1-228 | formyl | H | $CH_3$ | $CF(CF_3)_2$ | $C_2H_5$ | OH | 185-190 |
| I-1-229 | formyl | H | $CH_3$ | $CF(CF_3)_2$ | $C_2H_5$ | F | 70-74 |
| I-1-230 | formyl | H | $C_2H_5$ | $CF(CF_3)_2$ | $C_2H_5$ | H | 229-231 |
| I-1-231 | formyl | H | $CH_3$ | $CF(CF_3)_2$ | $C_2H_5$ | H | 221-220 |
| I-1-232 | formyl | H | $CH_3$ | $SC_3F_7$ | $C_2H_5$ | H | 139-141 |
| I-1-233 | formyl | H | I | $CF(CF_3)_2$ | I | H | 238 |
| I-1-234 | formyl | H | I | $CF(CF_3)_2$ | $n$-$C_3H_7$ | H | 208-210 |
| I-1-235 | formyl | H | Br | $CF(CF_3)_2$ | $n$-$C_3H_7$ | H | 201-203 |
| I-1-236 | formyl | H | $CH_3$ | $CF(CF_3)_2$ | H | H | 160-161 |
| I-1-237 | formyl | H | $CH_3$ | $CF(CF_3)_2$ | Br | H | 209-211 |
| I-1-238 | 2-fluoro-phenyl | H | I | $CF(CF_3)_2$ | $n$-$C_3H_7$ | H | 87-90 |
| I-1-239 | formyl | H | $CH_3$ | $CF(CF_3)_2$ | I | H | 190-192 |
| I-1-240 | formyl | H | $CH_3$ | $CF(CF_3)_2$ | Cl | H | 211-213 |
| I-1-241 | formyl | H | Cl | $CF(CF_3)_2$ | Cl | H | 213-214 |

TABLE 1-continued

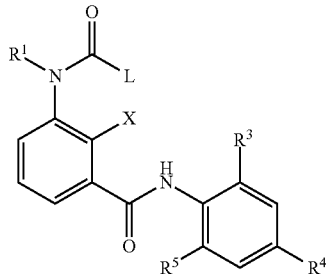

I-1

| No. | L | R¹ | R³ | R⁴ | R⁵ | X | M.p (° C.) |
|---|---|---|---|---|---|---|---|
| I-1-242 | formyl | H | Cl | $CF(CF_3)_2$ | $n\text{-}C_3H_7$ | H | 192-193 |
| I-1-243 | phenyl | H | I | $CF(CF_3)_2$ | $n\text{-}C_3H_7$ | H | 131-137 |
| I-1-244 | 4-cyano-phenyl | H | I | $CF(CF_3)_2$ | $n\text{-}C_3H_7$ | H | 125-131 |
| I-1-245 | 2-chloro-pyridin-3-yl | H | I | $CF(CF_3)_2$ | $n\text{-}C_3H_7$ | H | 119-124 |
| I-1-246 | 2-chloro-pyridin-3-yl | H | $CH_3$ | $CH(CF_3)_2$ | $C_2H_5$ | H | 1.4991 (nD) |
| I-1-247 | 2-fluoro-pyridin-3-yl | H | $CH_3$ | $CH(CF_3)_2$ | $C_2H_5$ | H | 164-169 |
| I-1-248 | 2-fluoro-phenyl | H | $CH_3$ | $CH(CF_3)_2$ | $C_2H_5$ | H | 198-201 |
| I-1-249 | phenyl | H | $CH_3$ | $CH(CF_3)_2$ | $C_2H_5$ | H | 182-186 |
| I-1-250 | 4-nitro-phenyl | H | $CH_3$ | $CH(CF_3)_2$ | $C_2H_5$ | H | 174-179 |
| I-1-251 | 2,5-difluoro-phenyl | H | $CH_3$ | $CH(CF_3)_2$ | $C_2H_5$ | H | 177-181 |
| I-1-252 | pyridine-3-yl | H | $CH_3$ | $CH(CF_3)_2$ | $C_2H_5$ | H | 1.4910 (nD) |
| I-1-253 | 2-chloro-pyridine-5-yl | H | $CH_3$ | $CH(CF_3)_2$ | $C_2H_5$ | H | 1.5005 (nD) |
| I-1-254 | 4-trifluoromethyl-pyridine-3-yl | H | $CH_3$ | $CH(CF_3)_2$ | $C_2H_5$ | H | 1.4629 (nD) |
| I-1-255 | $C_2H_5$ | H | I | $CF(CF_3)_2$ | I | H | >250 |
| I-1-256 | $i\text{-}C_3H_7$ | H | I | $CF(CF_3)_2$ | I | H | >250 |
| I-1-257 | 4-fluoro-benzyl | H | I | $CF(CF_3)_2$ | I | H | >250 |
| I-1-258 | $n\text{-}C_3H_7$ | H | I | $CF(CF_3)_2$ | I | H | >250 |
| I-1-259 | $sec\text{-}C_4H_9$ | H | I | $CF(CF_3)_2$ | I | H | >250 |
| I-1-260 | $i\text{-}C_4H_9$ | H | I | $CF(CF_3)_2$ | I | H | >250 |
| I-1-261 | $Cl(CH_2)_3$ | H | I | $CF(CF_3)_2$ | I | H | 235-236 |
| I-1-262 | phenyl | H | I | $COC_2H_5(CF_3)_2$ | I | H | 144-154 |
| I-1-263 | 2-fluoro-phenyl | H | I | $COC_2H_5(CF_3)_2$ | I | H | 1.5503 (nD) |
| I-1-264 | 3-fluoro-phenyl | H | I | $COC_2H_5(CF_3)_2$ | I | H | 138-145 |
| I-1-265 | 2-fluoro-pyridin-3-yl | H | I | $COC_2H_5(CF_3)_2$ | I | H | 1.5515 (nD) |
| I-1-266 | 2-chloro-pyridin-3-yl | H | I | $COC_2H_5(CF_3)_2$ | I | H | 1.5305 (nD) |
| I-1-267 | 2-chloro-pyridin-5-yl | H | I | $C(OC_2H_5)(CF_3)_2$ | I | H | 140-145 |
| I-1-268 | 2,6-dichloro-pyridin-3-yl | H | I | $C(OC_2H_5)(CF_3)_2$ | I | H | 1.5200 (nD) |
| I-1-269 | $Cl(CH_2)_2$ | H | I | $CF(CF_3)_2$ | $n\text{-}C_3H_7$ | H | 216-217 |
| I-1-270 | 2-chloro-pyridin-5-yl | H | I | $C(OCH_3)(CF_3)_2$ | I | H | 1.5032 (nD) |
| I-1-271 | $Cl(CH_2)_2$ | H | $CH_3$ | $CF(CF_3)_2$ | I | El | >250 |
| I-1-272 | $Cl(CH_2)_2$ | H | $CH_3$ | $CF(CF_3)_2$ | Cl | H | >250 |
| I-1-273 | $Cl(CH_2)_2$ | H | Br | $CF(CF_3)_2$ | Br | H | >250 |
| I-1-274 | phenyl | H | Br | $CF(CF_3)_2$ | $SCF_3$ | H | 81-87 |
| I-1-275 | 2-chloro-pyridin-3-yl | H | $CH_3$ | $CF(CF_3)_2$ | $CH_3$ | F | 1.4907 (nD) |
| I-1-276 | Cl(CH2)2 | H | $CH_3$ | $CF(CF_3)_2$ | $CH_3$ | H | NMR |
| I-1-277 | 2-fluoro-pyridin-3-yl | H | $CH_3$ | $CF(CF_3)_2$ | $CH_3$ | H | 170-172 |
| I-1-278 | 2-fluoro-pyridin-5-yl | H | $CH_3$ | $CF(CF_3)_2$ | $C_2H_5$ | F | 179-180 |
| I-1-279 | 2-chloro-pyridin-5-yl | H | $CH_3$ | $CF(CF_3)_2$ | $C_2H_5$ | F | 214-215 |
| I-1-280 | 2-fluoro-pyridin-3-yl | H | I | $CF(CF_3)_2$ | $C_2H_5$ | H | 98-100 |
| I-1-281 | 2-fluoro-pyridin-3-yl | H | I | $CF(CF_3)_2$ | $C_2H_5$ | H | 99-105 |
| I-1-282 | 2-fluoro-pyridin-3-yl | H | Br | $CF(CF_3)_2$ | $C_2H_5$ | H | 101-103 |
| I-1-283 | 2-fluoro-pyridin-3-yl | H | I | $CF(CF_3)_2$ | I | H | 121-124 |
| I-1-284 | 2-chloro-4-nitro-phenyl | H | I | $CF(CF_3)_2$ | $CH_3$ | H | 141-143 |
| I-1-285 | 2-chloro-3-nitro-phenyl | H | I | $CF(CF_3)_2$ | $CH_3$ | H | 139-143 |
| I-1-286 | 2-chloro-4-amino-phenyl | H | I | $CF(CF_3)_2$ | $CH_3$ | H | 137-139 |
| I-1-287 | 2-chloro-3-amino-phenyl | H | I | $CF(CF_3)_2$ | $CH_3$ | H | 159-162 |
| I-1-288 | 2-fluoro-phenyl | pyridin-3-yl-methyl | $CH_3$ | $CF(CF_3)_2$ | $C_2H_5$ | H | 197-199 |
| I-1-289 | 2-chloro-pyridin-3-yl | pyridin-3-yl-methyl | $CH_3$ | $CF(CF_3)_2$ | $C_2H_5$ | H | 184-186 |
| I-1-290 | 2-fluoro-phenyl | 2-fluoro-benzyl | $CH_3$ | $CF(CF_3)_2$ | $C_2H_5$ | H | 226 |
| I-1-291 | 2-chloro-pyridin-3-yl | 2-fluoro-benzyl | $CH_3$ | $CF(CF_3)_2$ | $C_2H_5$ | H | 197-198 |

TABLE 1-continued

I-1

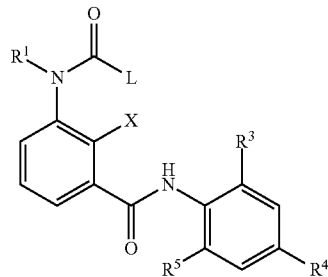

| No. | L | R¹ | R³ | R⁴ | R⁵ | X | M.p (° C.) |
|---|---|---|---|---|---|---|---|
| I-1-292 | 2-fluoro-phenyl | 2-chloro-pyridin-3-yl-methyl | CH₃ | CF(CF₃)₂ | C₂H₅ | H | 151-162 |
| I-1-293 | 4-nitro-phenyl | 2-chloro-pyridin-3-yl-methyl | CH₃ | CF(CF₃)₂ | C₂H₅ | H | 1.4963 (nD) |
| I-1-294 | 4-chloro-phenyl | 2-chloro-pyridin-3-yl-methyl | CH₃ | CF(CF₃)₂ | C₂H₅ | H | 125-127 |
| I-1-295 | 2-fluoro-phenyl | pyridin-2-yl-methyl | CH₃ | CF(CF₃)₂ | C₂H₅ | H | 220-222 |
| I-1-296 | 4-nitro-phenyl | pyridin-3-yl-methyl | CH₃ | CF(CF₃)₂ | C₂H₅ | H | 93-96 |
| I-1-297 | 4-chloro-phenyl | pyridin-3-yl-methyl | CH₃ | CF(CF₃)₂ | C₂H₅ | H | 158-160 |
| I-1-298 | 4-fluoro-phenyl | pyridin-3-yl-methyl | CH₃ | CF(CF₃)₂ | C₂H₅ | H | 185-187 |
| I-1-299 | 3-fluoro-phenyl | pyridin-3-yl-methyl | CH₃ | CF(CF₃)₂ | C₂H₅ | H | 195-196 |
| I-1-300 | 2,6-difluoro-phenyl | pyridin-3-yl-methyl | CH₃ | CF(CF₃)₂ | C₂H₅ | H | 202-203 |
| I-1-301 | 2,5-difluoro-phenyl | pyridin-3-yl-methyl | CH₃ | CF(CF₃)₂ | C₂H₅ | H | 190-192 |
| I-1-302 | 2-fluoro-pyridin-3-yl | pyridin-3-yl-methyl | CH₃ | CF(CF₃)₂ | C₂H₅ | H | 81-83 |
| I-1-303 | phenyl | pyridin-3-yl-methyl | CH₃ | CF(CF₃)₂ | C₂H₅ | H | 209-210 |
| I-1-304 | (E)-but-2-en-2-yl | pyridin-3-yl-methyl | CH₃ | CF(CF₃)₂ | C₂H₅ | H | 150-152 |
| I-1-305 | C₂H₅ | pyridin-3-yl-methyl | CH₃ | CF(CF₃)₂ | C₂H₅ | H | 127-134 |
| I-1-306 | 2-fluoro-pyridin-3-yl | pyridin-3-yl-methyl | CH₃ | CF(CF₃)₂ | C₂H₅ | H | 207-208 |
| I-1-307 | 4-cyano-phenyl | pyridin-3-yl-methyl | CH₃ | CF(CF₃)₂ | C₂H₅ | H | 228-230 |
| I-1-308 | phenyl | pyridin-3-yl-methyl | I | CF(CF₃)₂ | I | H | 178-181 |
| I-1-309 | 3-fluoro-phenyl | pyridin-3-yl-methyl | I | CF(CF₃)₂ | I | H | 1.5662 (nD) |
| I-1-310 | 4-fluoro-phenyl | pyridin-3-yl-methyl | I | CF(CF₃)₂ | I | H | 1.5135 (nD) |
| I-1-311 | 4-nitro-phenyl | pyridin-3-yl-methyl | I | CF(CF₃)₂ | I | H | 128-130 |
| I-1-312 | 3-fluoro-phenyl | pyridin-3-yl-methyl | Br | CF(CF₃)₂ | Br | H | 187-190 |
| I-1-313 | phenyl | pyridin-3-yl-methyl | Br | CF(CF)₂ | Br | H | 204-205 |
| I-1-314 | 2-chloro-pyridin-3-yl | pyridin-3-yl-methyl | Br | CF(CF₃)₂ | Br | H | 1.4947 (nD) |
| I-1-315 | 2-fluoro-pyridin-3-yl | CH₃ | CH₃ | CF(CF₃)₂ | CH₃ | F | |
| I-1-316 | 4-cyano-phenyl | CH₃ | CH₃ | CF(CF₃)₂ | CH₃ | F | |

TABLE 2

I-2

| No. | R¹ | R³ | R⁴ | R⁵ | Y | R⁶ | X | M.p (° C.) |
|---|---|---|---|---|---|---|---|---|
| I-2-1 | H | CH₃ | CF(CF₃)₂ | CH₃ | O | CH₂CCl₃ | F | 96-98 |
| I-2-2 | H | CH₃ | CF(CF₃)₂ | C₂H₅ | O | CH₂CCl₃ | H | 165-170 |
| I-2-3 | pyridin-3-yl-methyl | CH₃ | CF(CF₃)₂ | C₂H₅ | O | CH₂CCl₃ | H | 194-196 |
| I-2-4 | H | CH₃ | CF(CF₃)₂ | CH₃ | O | C₂H₅ | H | 1.4712 (nD) |
| I-2-5 | H | CH₃ | CF(CF₃)₂ | C₂H₅ | O | i-C₃H₇ | H | 186-190 |
| I-2-6 | H | I | CF(CF₃)₂ | I | O | C₂H₅ | H | 170-176 |
| I-2-7 | H | CH₃ | CF(CF₃)₂ | CH₃ | O | CH₂CCl₃ | H | NMR |
| I-2-8 | H | CH₃ | CF(CF₃)₂ | CH₃ | O | C₂H₅ | H | NMR |
| I-2-9 | H | CH₃ | CF(CF₃)₂ | CH₃ | O | i-C₃H₇ | H | NMR |
| I-2-10 | H | CH₃ | CF(CF₃)₂ | CH₃ | O | CH₂CF₃ | H | NMR |
| I-2-11 | H | I | CF(CF₃)₂ | I | O | CH₂CCl₃ | H | NMR |
| I-2-12 | 2-fluoro-benzyl | CH₃ | CF(CF₃)₂ | C₂H₅ | O | CH₂CCl₃ | H | 182-185 |
| I-2-13 | (2-chloropyridin-3-yl)methyl | CH₃ | CF(CF₃)₂ | C₂H₅ | O | CH₂CCl₃ | H | 1.4907 (nD) |
| I-2-14 | H | CH₃ | CF(CF₃)₂ | C₂H₅ | O | CH₃ | H | 195-197 |
| I-2-15 | pyridin-3-yl-methyl | I | CF(CF₃)₂ | I | O | C₂H₅ | H | 1.5360 (nD) |
| I-2-16 | H | I | COC₂F₅(CF₃)₂ | I | O | C₂H₅ | H | 157-161 |
| I-2-17 | CH3 | CH₃ | CF(CF₃)₂ | C₂H₅ | NCH₃ | CH₃ | H | 137-140 |
| I-2-18 | pyridin-3-yl-methyl | CH₃ | CF(CF₃)₂ | C₂H₅ | NCH₃ | CH₃ | H | 102-105 |
| I-2-19 | H | CH₃ | CF(CF₃)₂ | CH₃ | O | CH(CH₂F)₂ | F | |
| I-2-20 | H | CH₃ | CF(CF₃)₂ | CH₃ | O | (CH₂)₂Cl | F | |

| No. | NMR data |
|---|---|
| I-1-77 | 1H-NMR (CDCl3) δ: 2.36 (6H, s), 7.36 (2H, bs), 7.46-7.95 (8H, m), 7.96 (1H, bs), 8.27 (1H, bs) |
| I-1-155 | 1H-NMR (CDCl3) δ: 1.93-1.94 (3H, m), 2.34 (6H, s), 5.93-5.99 (1H, m), 7.00-7.03 (1H, m), 7.35 (2H, s), 7.44-7.47 (2H, m), 7.69-7.72 (3H, m), 8.26 (1H, s). |
| I-1-156 | 1H-NMR (CDCl3) δ: 1.68-1.73 (4H, m), 2.28 (6H, s), 2.41-2.43 (4H, m), 7.32 (2H, s), 7.40 (1H, t), 7.67-7.71 (2H, m), 7.97-8.00 (2H, m), 8.22 (1H, s). |
| I-1-157 | 1H-NMR (acetone-d6) δ: 1.16-1.21 (3H, m), 1.64-1.74 (4H, m), 2.36-2.46 (5H, m), 2.75-2.81 (6H, m), 6.04-6.05 (1H, m), 7.41-7.44 (3H, m), 7.68-7.70 (1H, m), 7.94-7.97 (1H, m), 8.30-8.30 (1H, m), 9.19-9.22 (1H, m). |
| I-1-158 | 1H-NMR (CDCl3) δ: 1.21-1.25 (3H, m), 2.32 (3H, s), 2.66-2.68 (2H, m), 7.06 (1H, d), 7.36-7.51 (6H, m), 7.68-7.80 (5H, m), 8.28 (2H, s). |
| I-1-159 | 1H-NMR (CDCl3) δ: 1.22 (4H, t), 1.83-1.87 (3H, m), 2.17 (3H, s), 2.35 (3H, s), 2.69-2.71 (2H, m), 6.57-6.60 (1H, m), 7.37 (2H, s), 7.49-7.51 (1H, m), 7.59 (1H, s), 7.69-7.71 (3H, m), 8.23 (1H, s). |
| I-1-160 | 1H-NMR (CDCl3) δ: 1.20-1.24 (3H, m), 1.82-1.96 (6H, m), 2.30 (3H, s), 2.67 (2H, q), 5.73-5.75 (1H, m), 7.38-7.41 (3H, m), 7.69-7.72 (3H, m), 8.03 (1H, s), 8.26 (1H, s). |
| I-1-161 | 1H-NMR (CDCl3) δ: 1.24-1.27 (3H, m), 2.31 (3H, br s), 2.65-2.68 (2H, m), 6.31 (1H, d), 7.34-7.38 (3H, m), 7.63-7.67 (1H, m), 7.74-7.78 (1H, m), 8.00-8.03 (1H, m), 8.16-8.19 (1H, m), 8.40-8.43 (1H, m). |
| I-1-162 | 1H-NMR (CDCl3) δ: 0.89-0.91 (2H, m), 1.11-1.12 (2H, m), 1.22 (3H, t), 2.34 (3H, s), 2.68-2.70 (2H, m), 7.36 (2H, s), 7.47-7.49 (1H, m), 7.62-7.68 (4H, m), 8.20 (1H, s). |
| I-1-163 | 1H-NMR (CDCl3) δ: 1.17 (3H, t), 2.16 (3H, s), 2.27 (3H, s), 2.65 (2H, q), 7.30-7.43 (9H, m), 7.64-7.66 (1H, m), 7.76-7.79 (1H, m), 7.98 (1H, s), 8.06 (1H, s), 8.24 (1H, s). |
| I-1-164 | 1H-NMR (acetone-d6) δ: 1.41-1.44 (3H, m), 1.55-1.55 (3H, m), 2.01 (8H, m), 6.19-6.22 (1H, m), 7.07-7.10 (3H, m), 7.36-7.38 (1H, m), 7.61-7.64 (1H, m), 7.96-7.97 (1H, m), 8.77 (1H, s), 8.87 (1H, s). |
| I-1-165 | 1H-NMR (CDCl3) δ: 1.86-1.88 (3H, m), 1.99-1.99 (3H, m), 2.36 (5H, m), 2.72 (3H, q), 6.63-6.65 (1H, m), 7.31-7.33 (1H, m), 7.38 (2H, s), 7.72-7.82 (3H, m), 8.52-8.52 (1H, m). |
| I-1-166 | 1H-NMR (CDCl3) δ: 1.09-1.11 (3H, m), 1.21-1.24 (3H, m), 1.97 (3H, d), 2.24-2.26 (2H, m), 2.35 (3H, s), 2.69-2.71 (2H, m), 6.45-6.49 (1H, m), 7.49-7.62 (7H, m), 8.23 (1H, s). |

-continued

| No. | NMR data |
|---|---|
| I-1-167 | 1H-NMR (CDCl3) δ: 1.20-1.25 (3H, m), 1.64-1.74 (4H, m), 2.24-2.26 (2H, m), 2.35-2.37 (2H, m), 2.70 (2H, q), 6.80 (1H, s), 7.36 (2H, s), 7.47-7.49 (1H, m), 7.57 (1H, s), 7.71 (3H, dd), 8.23 (1H, s). |
| I-1-168 | 1H-NMR (CDCl3) δ: 1.22 (3H, t), 2.06-2.08 (2H, m), 2.34 (3H, s), 2.56-2.58 (2H, m), 2.67-2.71 (4H, m), 6.72 (1H, s), 7.36 (2H, s), 7.49-7.52 (2H, m), 7.67-7.76 (3H, m), 8.24 (1H, s). |
| I-1-169 | 1H-NMR (CDCl3) δ: 1.09 (3H, t), 1.96 (3H, s), 2.17-2.27 (2H, m), 2.34 (6H, s), 6.46-6.47 (1H, m), 7.35 (2H, s), 7.47 (1H, t), 7.67-7.70 (3H, m), 7.78 (1H, s), 8.24 (1H, s). |
| I-1-170 | 1H-NMR (CDCl3) δ: 1.66-1.74 (4H, m), 2.25-2.37 (4H, m), 6.78-6.82 (1H, m), 7.35 (2H, s), 7.47-7.50 (1H, m), 7.57 (1H, s), 7.68-7.70 (2H, m), 7.79 (1H, s), 8.25 (1H, s). |
| I-1-171 | 1H-NMR (CDCl3) δ: 1.81-1.83 (3H, m), 1.94 (3H, s), 6.56-6.58 (1H, m), 7.44 (1H, t), 7.70-7.80 (2H, m), 8.09 (2H, s), 8.22-8.22 (1H, m), 8.29 (1H, s). |
| I-1-172 | 1H-NMR (acetone-d6) δ: 1.88-1.91 (3H, m), 2.03-2.04 (3H, m), 6.56-6.58 (1H, m), 7.45-7.50 (1H, m), 7.78-7.80 (1H, m), 8.01-8.02 (1H, m), 8.27-8.28 (2H, m), 8.36 (1H, d), 9.15 (1H, s), 9.73 (1H, s). |
| I-1-173 | 1H-NMR (CDCl3) δ: 7.20-7.30 (3H, m), 7.49-7.54 (2H, m), 7.79-7.92 (2H, m), 8.11-8.14 (3H, m), 8.31-8.34 (2H, m), 8.65-8.70 (1H, m). |
| I-1-174 | 1H-NMR (CDCl3) δ: 7.20-7.28 (3H, m), 7.45-7.55 (2H, m), 7.76-7.92 (3H, m), 8.10-8.13 (1H, m), 8.32-8.32 (2H, m), 8.65-8.71 (1H, m). |
| I-1-175 | 1H-NMR (acetone-d6) δ: 6.89-6.92 (2H, m), 7.20-7.57 (7H, m), 8.21-8.39 (3H, m), 9.45-9.48 (1H, m). |
| I-1-176 | 1H-NMR (CDCl3) δ: 7.47-7.59 (2H, m), 7.78-7.80 (1H, m), 7.96-7.99 (2H, m), 8.08-8.12 (2H, m), 8.18-8.27 (3H, m), 8.88-8.92 (1H, m). |
| I-1-177 | 1H-NMR (acetone-d6) δ: 1.87-2.66 (6H, m), 6.69-6.70 (1H, m), 7.42-8.32 (6H, m), 9.12 (1H, s), 9.69 (1H, s). |
| I-1-178 | 1H-NMR (CDCl3) δ: 7.19-7.37 (2H, m), 7.52-7.60 (2H, m), 7.80-7.91 (4H, m), 8.12-8.17 (2H, m), 8.33-8.36 (1H, m), 8.61-8.66 (1H, m). |
| I-1-188 | 1H-NMR (CDCl3) δ: 1.23 (3H, t), 2.36 (3H, s), 2.71 (2H, q), 7.12 (1H, t), 7.27-7.44 (4H, m), 7.51-7.61 (2H, m), 7.69-7.77 (2H, m), 7.84 (1H, d), 8.30 (1H, s). |
| I-1-189 | 1H-NMR (CDCl3) δ: 1.23 (3H, t), 2.32 (3H, s), 2.68 (2H, q), 7.18-7.26 (1H, m), 7.34 (1H, t), 7.45 (2H, s), 7.50-7.62 (3H, m), 7.73 (1H, d), 7.87 (1H, d), 8.15-8.21 (1H, m), 8.33 (1H, s), 8.63 (1H, d). |
| I-1-206 | 1H-NMR (DMSO-d6) δ: 7.53-7.63 (3H, m), 7.82 (1H, d), 8.01-8.07 (3H, m), 8.29 (2H, s), 8.35 (1H, s), 10.53 (1H, s), 10.59 (1H, s). |
| I-1-208 | 1H-NMR (DMSO-d6) δ: 7.50-7.60 (2H, m), 7.82 (1H, d), 7.97 (1H, d), 8.32-8.24 (4H, m), 8.41 (1H, d), 10.62 (1H, s), 10.80 (1H, s). |
| I-1-209 | 1H-NMR (CDCl3) δ: 7.45 (1H, dd), 7.55 (1H, t), 7.78 (1H, d), 7.96 (1H, d), 8.02 (1H, s), 8.09 (2H, s), 8.22 (1H, d), 8.32 (2H, d), 8.78 (1H, d), 9.14 (1H, s). |
| I-1-276 | 1H-NMR (CDCl3) δ: 2.35 (6H, s), 2.59 (2H, t, J = 6.6 Hz), 3.67 (2H, t, J = 6.6 Hz), 7.28-7.54 (5H, m), 7.65-7.77 (2H, m), 8.17 (1H, bs) |
| I-1-211 | 1H-NMR (DMSO-d6) δ: 7.55-7.64 (3H, m), 7.83 (1H, d), 8.09-8.02 (3H, m), 8.30 (2H, s), 8.37 (1H, s), 10.54 (1H, s), 10.60 (1H, s). |
| I-2-7 | 1H-NMR (CDCl3) δ: 2.35 (6H, s), 4.85 (2H, s), 7.16 (1H, bs), 7.35 (2H, bs), 7.46-7.69 (4H, m), 8.05 (1H, bs) |
| I-2-8 | 1H-NMR (CDCl3) δ: 1.33 (3H, t), 2.35 (6H, s), 4.25 (2H, q), 6.75 (1H, bs), 7.35 (2H, bs), 7.41-7.64 (4H, m), 8.02 (1H, bs) |
| I-2-9 | 1H-NMR (CDCl3) δ: 1.32 (6H, t), 2.35 (6H, s), 5.04 (1H, sep), 6.68 (1H, bs), 7.27-7.65 (6H, m), 8.03 (1H, bs) |
| I-2-10 | 1H-NMR (CDCl3) δ: 2.32 (6H, s), 4.57 (2H, q), 7.10 (1H, bs), 7.35 (2H, bs), 7.42-7.69 (4H, m), 8.00 (1H, bs) |
| I-2-11 | 1H-NMR (CDCl3) δ: 4.84 (2H, s), 7.38-7.41 (1H, m), 7.48-7.50 (1H, m), 7.71-7.73 (2H, m), 8.04-8.08 (4H, m). |

The present invention will be further described in the following examples. However. these examples are not intended to limit the scope of the present application.

Example No. 1

*Boophilus microplus*—Test (Injection)
Solvent: Dimethyl Sulfoxide

To produce a suitable preparation of active compound, 10 mg of active compound are dissolved in 0.5 ml solvent, and the concentrate is diluted with water to the desired concentration.

Five adult engorged female ticks (*Boophilus microplus*) are injected with compound solution into the abdomen. Ticks are transferred into replica plates and incubated in a climate chamber for a period of time. Egg deposition of fertile eggs is monitored.

After the specified period of time, mortality in % is determined. 100% means that all eggs are infertile; 0% means that all eggs are fertile.

In this test for example, the following compounds from the preparation examples showed good activity oft 80% at application rate of 20 μg/animal:

Example number I-1-5, I-1-6, I-1-7, I-1-15, I-1-20, I-1-24, I-1-29, I-1-30, I-1-32, I-1-35, I-1-36, I-1-39, I-1-40, I-1-41, I-1-42, I-1-43, I-1-44, I-1-45, I-1-46, I-1-49, I-1-51, I-1-52, I-1-54, I-1-55, I-1-56, I-1-57, I-1-58, I-1-59, I-1-60, I-1-61, I-1-62, I-1-63, I-1-64, I-1-66, I-1-72, I-1-75, I-1-77, I-1-88, I-1-134, I-1-139, I-1-149, I-1-150, I-1-151, I-1-154, I-1-155, I-1-156, I-1-157, I-1-158, I-1-159, I-1-160, I-1-161, I-1-162, I-1-163, I-1-164, I-1-165, I-1-166, I-1-167, I-1-168, I-1-169, I-1-170, I-1-171, I-1-173, I-1-174, I-1-175, I-1-176, I-1-177, I-1-178, I-1-179, I-1-180, I-1-181, I-1-182, I-1-183, I-1-184, I-1-185, I-1-186, I-1-187, I-1-188, I-1-189, I-1-190, I-1-191, I-1-192, I-1-193, I-1-194, I-1-195, I-1-196, I-1-197, I-1-198, I-1-199, I-1-200, I-1-201, I-1-202, I-1-203, I-1-204, I-1-205, I-1-206, I-1-207, I-1-208, I-1-209, I-1-210, I-1-211, I-1-212, I-1-213, 1-1-214, I-1-215, I-1-216, I-1-217, I-1-218, I-1-219, I-1-221, I-1-222, I-1-223, I-1-224, I-1-225, I-1-226, I-1-227, I-1-228, I-1-229, I-1-230, I-1-231, I-1-233, I-1-234, I-1-235, I-1-236, I-1-237, I-1-238, I-1-239, I-1-240, I-1-241, I-1-242, I-1-243, I-1-244, I-1-245, I-1-246, I-1-247, I-1-248, I-1-249, I-1-250, I-1-251, I-1-252, I-1-253, I-1-254, I-1-255, I-1-256, I-1-257, I-1-258 I-1-259, I-1-260, I-1-261, I-1-262, I-1-263, I-1-264, I-1-265, I-1-266, I-1-267, I-1-268, I-1-269, I-1-270, I-1-271, I-1-272, I-1-273, I-1-274, I-1-275, I-1-276, I-1-277, I-1-278, I-1-279, I-1-280, I-1-281, I-1-282, I-1-283, I-1-284, I-1-285, I-1-286, I-1-287, I-1-288, I-1-289, I-1-290, I-1-291, I-1-292, I-1-293, I-1-294, I-1-295, I-1-296, I-1-297, I-1-298, I-1-299, I-1-300, I-1-301, I-1-302, I-1-303, I-1-304, I-1-305, I-1-306, I-1-307, I-1-308, I-1-309, I-1-310, I-1-311, I-1-312, I-1-313, I-1-314, I-2-1, I-2-2, I-2-3, I-2-4, I-2-5, I-2-6, I-2-7, I-2-8, I-2-17, I-2-18

Example No. 2

*Ctenocephalides felis*—Test (CTECFE)
Solvent: Dimethyl Sulfoxide

To produce a suitable preparation of active compound, 10 mg of active compound are dissolved in 0.5 ml solvent, and the concentrate is diluted with cattle blood to the desired concentration.

Approximately 10 to 15 adult unfed (*Ctenocepahlides felis*) are placed in flea chambers. The blood chamber, sealed with parafilm on the bottom are filled with cattle blood supplied with compound solution and placed on top of the flea chamber, so that the fleas are able to suck the blood. The blood chamber is heated to 37° C. whereas the flea chamber is kept at room temperature.

After the specified period of time, mortality in % is determined. 100% means that all the fleas have been killed; 0% means that none of the fleas have been killed.

In this test for example, the following compounds from the preparation examples showed good activity of ≥80% at application rate of 100 ppm:

Example number I-1-5, I-1-6, I-1-7, I-1-30, I-1-32, I-1-35, I-1-36, I-1-40, I-1-42, I-1-46, I-1-49, I-1-51, I-1-52, I-1-54, I-1-55, I-1-56, I-1-57, I-1-59, I-1-61, I-1-62, I-1-63, I-1-66, I-1-72, I-1-75, I-1-88, I-1-134, I-1-139, I-1-149, I-1-150, I-1-151, I-1-155, I-1-156, I-1-159, I-1-162, I-1-164, I-1-165, I-1-166, I-1-167, I-1-168, I-1-169, I-1-170, I-1-171, I-1-173, I-1-174, I-1-175, I-1-176, I-1-177, I-1-178, I-1-180, I-1-181, I-1-182, I-1-183, I-1-184, I-1-185, I-1-186, I-1-187, I-1-188, I-1-189, I-1-191, I-1-192, I-1-193, I-1-194, I-1-195, I-1-196, I-1-197, I-1-198, I-1-199, I-1-200, I-1-201, I-1-203, I-1-204, I-1-206, I-1-207, I-1-208, I-1-209, I-1-210, I-1-211, I-1-212, I-1-213, I-1-214, I-1-217, I-1-218, I-1-219, I-1-220, I-1-221, I-1-222, 1I-1-223, I-1-224, I-1-226, I-1-227, I-1-229, I-1-230, I-1-231, I-1-233, I-1-234, I-1-235, I-1-238, I-1-241, I-1-242, I-1-243, I-1-244, I-1-245, I-1-246, I-1-247, I-1-248, I-1-249, I-1-250, I-1-251, I-1-252, I-1-253, I-1-254, I-1-255, I-1-256, I-1-257, I-1-258 I-1-259, I-1-260, I-1-261, I-1-262, I-1-263, I-1-264, I-1-265, I-1-266, I-1-267, I-1-269, I-1-271, I-1-274, I-1-275, I-1-276, I-1-277, I-1-278, I-1-279, I-1-280, I-1-281, I-1-282, I-1-283, I-1-284, I-1-287, I-1-288, I-1-289, I-1-292, I-1-293, I-1-295, I-1-296, I-1-297, I-1-298, I-1-299, I-1-300, I-1-301, I-1-302, I-1-304, I-1-306, I-1-307, I-1-308, I-1-309, I-1-310, I-1-311, I-1-312, I-1-313, I-1-314, I-2-1, I-2-2, I-2-4, I-2-5, I-2-6, I-2-7, I-2-8

Example No. 3

*Lucillia cuprina*—Test
Solvent: Dimethyl Sulfoxide

To produce a suitable preparation of active compound, 10 mg of active compound are dissolved in 0.5 ml solvent, and the concentrate is diluted with water to the desired concentration.

Approximately 20-30 (*Lucilia cuprina* larvae) are transferred into a test tube containing 1 cm³ of minced horse meat and 0.5 ml aqueous dilution of test compound.

After the specified period of time, mortality in % is determined. 100% means that all the larvae have been killed; 0% means that none of the larvae have been killed.

In this test for example, the following compounds from the preparation examples showed good activity of ≥80% at application rate of 100 ppm:

Example number I-1-5, I-1-6, I-1-7, I-1-15, I-1-24, I-1-29, I-1-30, I-1-32, I-1-35, I-1-36, I-1-39, I-1-40, I-1-41, I-1-42, I-1-43, I-1-44, I-1-45, I-1-46, I-1-49, I-1-51, I-1-52, I-1-54, I-1-55, I-1-56, I-1-57, I-1-58, I-1-59, I-1-60, I-1-61, I-1-62, I-1-63, I-1-64, I-1-66, I-1-72, I-1-75, I-1-77, I-1-88, I-1-134, I-1-139, I-1-149, I-1-150, I-1-151, I-1-154, I-1-155, I-1-156, I-1-159, I-1-160, I-1-164, I-1-165, I-1-166, I-1-167, I-1-168, I-1-170, I-1-171, I-1-173, I-1-174, I-1-175, I-1-176, I-1-177, I-1-178, I-1-179, I-1-180, I-1-181, I-1-182, I-1-183, I-1-184, I-1-185, I-1-186, I-1-187, I-1-188, I-1-189, I-1-190, I-1-191, I-1-192, I-1-193, I-1-194, I-1-195, I-1-196, I-1-197, I-1-198, I-1-199, I-1-200, I-1-204, I-1-206, I-1-207, I-1-208, I-1-209, I-1-210, I-1-211, I-1-213, I-1-214, I-1-215, I-1-216, I-1-218, I-1-219, I-1-220, I-1-221, I-1-222, I-1-223, I-1-224, I-1-225, I-1-226, I-1-227, I-1-229, I-1-230, I-1-231, I-1-232, I-1-233, I-1-234, I-1-235, I-1-237, I-1-238, I-1-239, I-1-240, I-1-241, I-1-242, I-1-243, I-1-244, I-1-245, I-1-246, I-1-247, I-1-248, I-1-249, I-1-250, I-1-251, I-1-252, I-1-255, I-1-256, I-1-257, I-1-258 I-1-259, I-1-260, I-1-261, I-1-262, I-1-263, I-1-264, I-1-265, I-1-266, I-1-267, I-1-268, I-1-269, I-1-270, I-1-271, I-1-272, I-1-273, I-1-274, I-1-275, I-1-276, I-1-277, I-1-278, I-1-279, I-1-280, I-1-281, I-1-282, I-1-283, I-1-284, I-1-285, I-1-286, I-1-287, I-1-288, I-1-289, I-1-291, I-1-292, I-1-293, I-1-294, I-1-295, I-1-296, I-1-297, I-1-298, I-1-299, I-1-300, I-1-301, I-1-302, I-1-303, I-1-304, I-1-306, I-1-308, I-1-309, I-1-310, I-1-311, I-1-312, I-1-313, I-1-314, I-2-1, I-2-2, I-2-3, I-2-4, I-2-5, I-2-6, I-2-7, I-2-8

Example No. 4

*Musca domestica*—Test
Solvent: Dimethyl Sulfoxide

To produce a suitable preparation of active compound, 10 mg of active compound are dissolved in 0.5 ml solvent, and the concentrate is diluted with water to the desired concentration.

Prior to the assay, a piece or kitchen sponge is soaked with a mixture of sugar and compound solution and placed into a container. 10 adults (*Musca domestica*) are placed into the container and closed with a perforated lid.

After the specified period of time, mortality in % is determined. 100% means that all the flies have been killed; 0% means that none of the flies have been killed.

In this test for example, the following compounds from the preparation examples showed good activity of ≥80% at application rate of 100 ppm:

Example number I-1-5, I-1-6, I-1-7, I-1-32, I-1-44, I-1-52, I-1-54, I-1-62, I-1-63, I-1-72, I-1-75, I-1-139, I-1-173, I-1-174, I-1-175, I-1-176, I-1-177, I-1-178, I-1-185, I-1-191, I-1-193, I-1-194, I-1-195, I-1-196, I-1-197, I-1-199, I-1-208, I-1-209, I-1-210, I-1-222, I-1-229, I-1-238, I-1-243, I-1-244, I-1-245, I-1-246, I-1-247, I-1-255, I-1-258, I-1-260, I-1-261, I-1-262, I-1-263, I-1-264, I-1-265, I-1-266, I-1-267, I-1-269, I-1-271, I-1-274, I-1-275, I-1-277, I-1-278, I-1-279, I-1-280, I-1-281, I-1-282, I-1-283, I-1-284, I-1-285, I-1-288, I-1-289, I-1-292, I-1-300, I-1-302, I-1-306, I-1-308, I-1-309, I-1-310, I-1-311, I-1-312, I-1-313, I-1-314, I-2-1, I-2-2, I-2-3, I-2-4, I-2-6, I-2-7

Example No. 5

*Boophilus microplus* (Dip)

Solvent: Dimethyl Sulfoxide

To produce a suitable preparation of active compound, 10 mg of active compound are dissolved in 0.5 ml solvent, and the concentrate is diluted with water to the desired concentration.

Eight to ten adult engorged female *Boophilus microplus* ticks are placed in perforated plastic beakers and immersed in aqueous compound solution for one minute. Ticks are transferred to a filter paper in a plastic tray and incubated in a climate chamber for a period of time. Egg deposition of fertile eggs is monitored.

After the specified period of time, mortality in % is determined. 100% means that all eggs are infertile; 0% means that all eggs are fertile.

In this test for example, the following compounds from the preparation examples showed good activity of ≥80% at application rate of 100 ppm:

Example No. I-1-5, I-1-6, I-a-54, I-1-192, I-1-194, I-1-195, I-1-238, I-1-245, I-1-246, I-1-260, I-1-274, I-1-275, I-1-278, I-1-280, I-1-281, I-1-282, I-1-283

Example No. 6

*Amblyomma hebraeum*—Test (AMBYHE)

Solvent: Dimethylsulfoxide

To produce a suitable preparation of active compound, 1 part by weight of active compound is mixed with the stated amount of solvent, and the concentrate is diluted with containing solvent to the desired concentration.

Nymphs of the tick *Amblyomma hebraeum* are placed in perforated plastic beakers and immersed in aqueous compound solution for one minute. Ticks are transferred to a filter paper in a Petri dish and incubated in a climate chamber for 42 days.

After the specified period of time, mortality in % is determined. 100% means that all the ticks have been killed; 0% means that none of the ticks have been killed.

In this test for example, the following compounds from the preparation examples showed good activity of ≥80% at application rate of 100 ppm:

Example No. I-1-5, I-1-280, I-1-281, I-1-282

When not mentioned otherwise the tested compounds or compositions were administered in a suitable formulation.

What is claimed is:

1. A method for preventing an infection with diseases transmitted through acari selected from the group consisting of *Amblyomma americanum, Dermacentor variabilis, Dermacentor reticulatus*, and *Rhipicephalus sanguineus*, comprising administering orally, topically, or parenterally to a domestic animal, companion animal, or agricultural livestock in need of said preventing a compound having a formula (I-1)

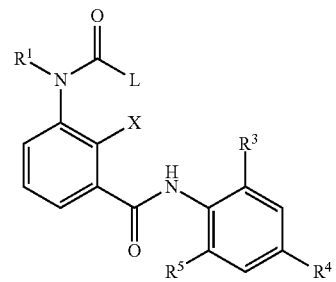

wherein

X represents a hydrogen atom or a halogen atom;

$R^1$ represents a hydrogen atom or a $C_1$-$C_6$ alkyl group;

$R^3$ and $R^5$ represent, independent from each other, a halogen atom, a $C_1$-$C_4$ alkyl group, or a $C_1$-$C_4$ haloalkyl group;

$R^4$ represents a $C_1$-$C_4$ haloalkyl group;

L represents a pyridin-3-yl group, optionally mono-substituted in the 6 position or di-substituted in the 4 position and 6 position with one or more substituents selected from the group consisting of a halogen atom, a $C_1$-$C_4$ alkyl group, and a $C_1$-$C_4$ haloalkyl group or a phenyl group substituted with one or more substituents selected from the group consisting of a halogen atom, a $C_1$-$C_4$ alkyl group, and a $C_1$-$C_4$ haloalkyl group.

2. The method of claim 1, wherein L represents pyridin-3-yl, which is substituted in the 6-position.

3. The method of claim 1, wherein L represents pyridin-3-yl, which is substituted in the 4-position and 6-position.

4. The method of claim 1, wherein L represents a pyridyl group selected from the group consisting of 6-fluoropyridin-3-yl, 4,6-difluoropyridin-3-yl, 6-chloropyridin-3-yl, and 6-chloro-4-(trifluoromethyl)pyridin-3-yl.

5. The method of claim 1, wherein L represents a pyridyl group selected from the group consisting of 6-fluoropyridin-3-yl, and 6-chloropyridin-3-yl, and 6-chloro-4-(trifluoromethyl)pyridin-3-yl.

6. The method of claim 1, wherein said acari is selected from the group consisting of *Amblyomma americanum, Dermacentor variabilis*, and *Dermacentor reticulatus*.

7. The method of claim 1, wherein said acari is *Dermacentor variabilis*.

8. The method of claim 1, comprising administering orally to a domestic animal, companion animal, or agricultural livestock in need of said preventing the compound of formula (I-1).

9. The method of claim 1, comprising administering topically to a domestic animal, companion animal, or agricultural livestock in need of said preventing the compound of formula (I-1).

10. The method of claim 1, comprising administering parenterally to a domestic animal, companion animal, or agricultural livestock in need of said preventing the compound of formula (I-1).

11. The method of claim 5, wherein

X represents fluorine;

$R^1$ represents hydrogen;

$R^3$ represents $CH_3$;

$R^5$ represents $C_2H_5$;

$R^4$ represents $CF(CF_3)_2$; and

L represents a 6-fluoropyridin-3-yl.

12. The method of claim 1, wherein L represents a 6-halopyridin-3-yl group.

13. The method of claim 1, wherein L represents a phenyl group substituted with one or more substituents selected from the group consisting of a halogen atom, a $C_1$-$C_4$ alkyl group, and a $C_1$-$C_4$ haloalkyl group.

* * * * *